(12) United States Patent
Yu et al.

(10) Patent No.: US 11,612,399 B2
(45) Date of Patent: **\*Mar. 28, 2023**

(54) IMPLANTABLE NERVE GUIDANCE CONDUITS HAVING POLYMER FIBER GUIDANCE CHANNEL

(71) Applicant: The Trustees of the Stevens Institute of Technology, Hoboken, NJ (US)

(72) Inventors: Xiaojun Yu, Fishers, IN (US); Munish B. Shah, Galloway, NJ (US); Wei Chang, New York, NY (US)

(73) Assignee: THE TRUSTEES OF THE STEVENS INSTITUTE OF TECHNOLOGY, Hoboken, NJ (US)

( * ) Notice: Subject to any disclaimer, the term of this patent is extended or adjusted under 35 U.S.C. 154(b) by 950 days.

This patent is subject to a terminal disclaimer.

(21) Appl. No.: 16/448,550

(22) Filed: Jun. 21, 2019

(65) Prior Publication Data

US 2019/0328393 A1  Oct. 31, 2019

Related U.S. Application Data

(63) Continuation of application No. 15/451,039, filed on Mar. 6, 2017, now Pat. No. 10,363,041, which is a continuation-in-part of application No. 14/313,384, filed on Jun. 24, 2014, now Pat. No. 9,585,666.

(60) Provisional application No. 62/315,755, filed on Mar. 31, 2016, provisional application No. 61/838,553, filed on Jun. 24, 2013.

(51) Int. Cl.
| | |
|---|---|
| *A61B 17/11* | (2006.01) |
| *A61L 27/18* | (2006.01) |
| *A61L 27/50* | (2006.01) |
| *A61L 27/56* | (2006.01) |
| *A61B 17/00* | (2006.01) |

(52) U.S. Cl.
CPC .......... *A61B 17/1128* (2013.01); *A61L 27/18* (2013.01); *A61L 27/50* (2013.01); *A61L 27/56* (2013.01); *A61B 2017/00526* (2013.01); *A61B 2017/1132* (2013.01); *A61L 2400/12* (2013.01); *A61L 2430/32* (2013.01)

(58) Field of Classification Search
CPC ...... A61B 17/1128; A61B 2017/00526; A61B 2017/1132; A61L 27/18; A61L 27/50; A61L 27/56; A61L 2430/32; A61L 2400/12
See application file for complete search history.

(56) References Cited

U.S. PATENT DOCUMENTS

| | | | |
|---|---|---|---|
| 9,585,666 B2 * | 3/2017 | Yu | A61B 17/1128 |
| 10,363,041 B2 * | 7/2019 | Yu | A61B 17/1128 |

\* cited by examiner

*Primary Examiner* — Shirley V Gembeh
(74) *Attorney, Agent, or Firm* — Lewis Roca Rothgerber Christie LLP

(57) ABSTRACT

A nerve guidance conduit includes one or more guidance channels formed as porous polymeric structures. The guidance channels are within an outer tubular structure that includes randomly-oriented nanofibers. The guidance channels may have electrospun nanofibers on their inner and outer surfaces in a parallel alignment with the guidance channels. Such aligned nanofibers may also be present on the inner surface of the outer tubular structure. The outer surfaces of the guidance channels and the inner surface of the tubular structure define additional guidance channels. Such a nerve guidance conduit provides augmented surface areas for providing directional guidance and enhancing peripheral nerve regeneration. The structure also has the mechanical and nutrient transport requirements required over long regeneration periods.

20 Claims, 16 Drawing Sheets

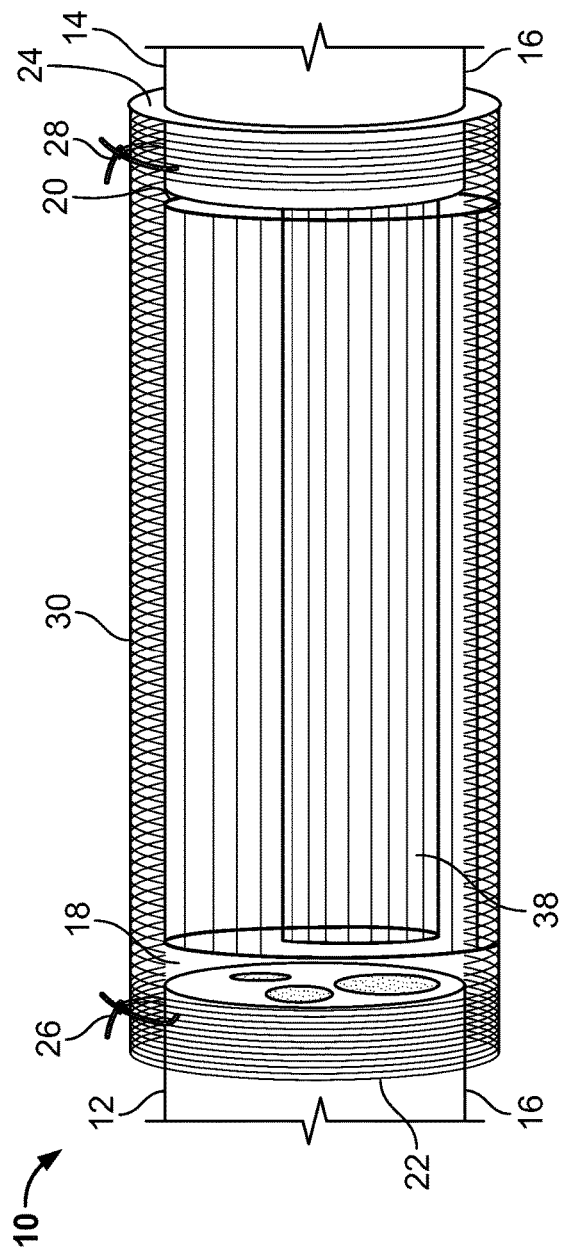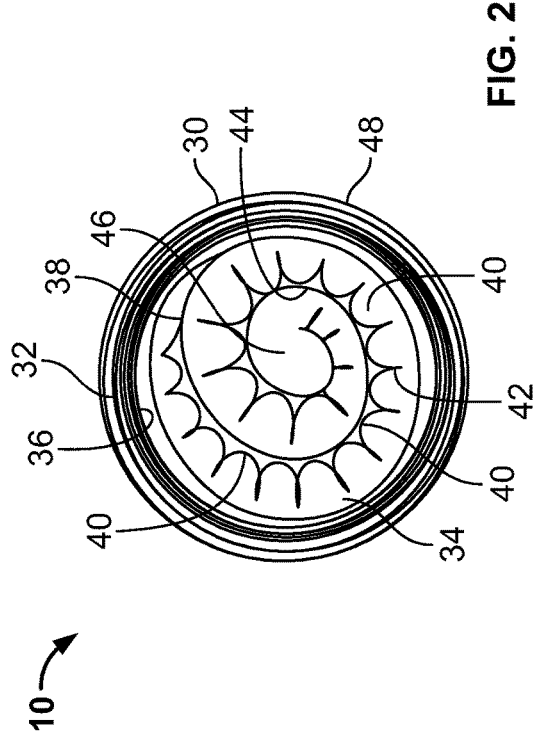

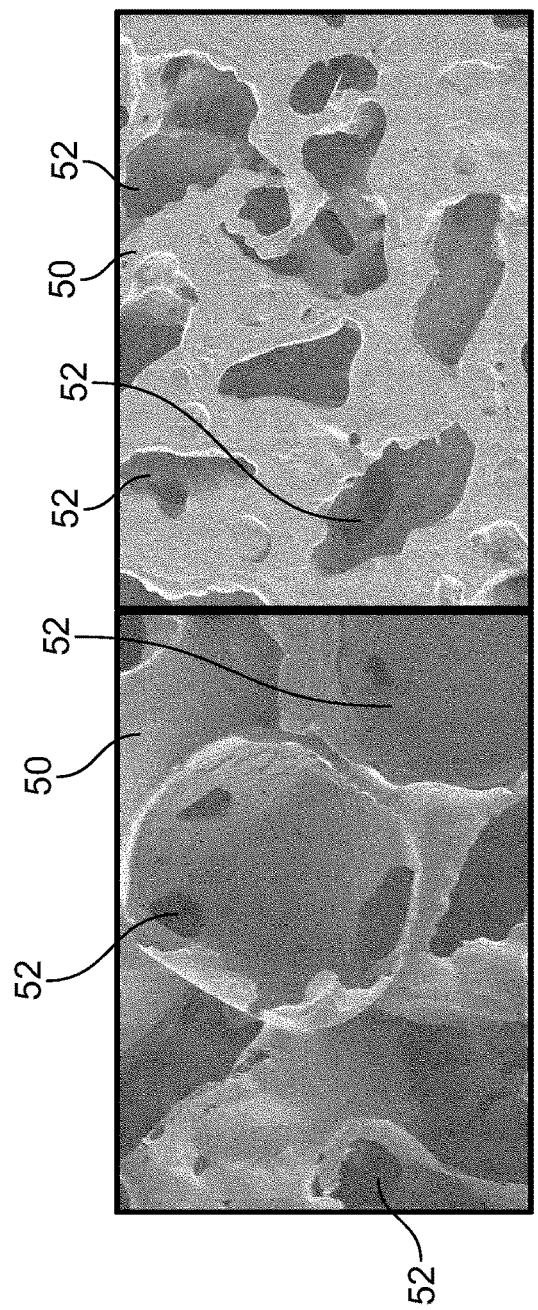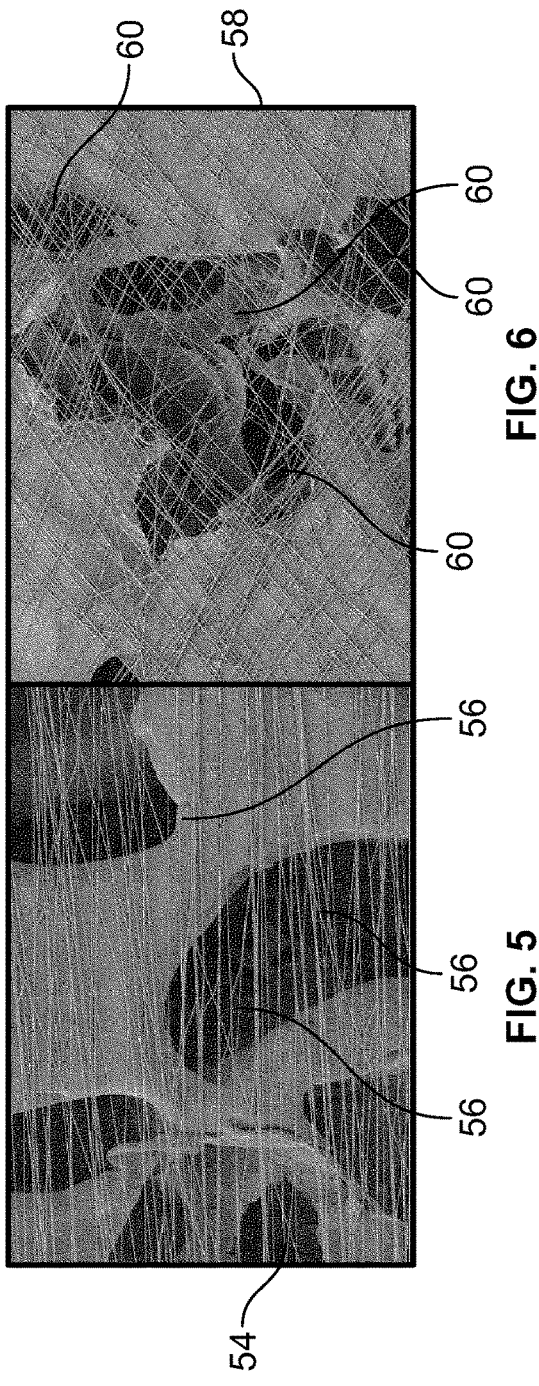
FIG. 3
FIG. 4
FIG. 5
FIG. 6

IMPLANTABLE NERVE GUIDANCE CONDUITS HAVING POLYMER FIBER GUIDANCE CHANNEL

CROSS-REFERENCE TO RELATED APPLICATIONS

This application is a continuation of U.S. application Ser. No. 15/451,039 filed Mar. 6, 2017, which claims the benefit of U.S. Provisional Application No. 62/315,755 filed Mar. 31, 2016, and which is a continuation-in-part of U.S. application Ser. No. 14/313,384 filed Jun. 24, 2014, (now U.S. Pat. No. 9,585,666 issued Mar. 7, 2017), which claims the benefit of U.S. Provisional Application No. 61/838,553 filed Jun. 24, 2013, the entire disclosures of each of the aforesaid applications are incorporated herein by reference.

STATEMENT REGARDING FEDERALLY SPONSORED RESEARCH

This invention was made with government support under Grant Numbers NS074404 and NS058595 awarded by The National Institutes of Health and Grant Numbers W81XWH-13-1-0320 and W81WH-13-0-2301 awarded by the ARMY/MRMC—Medical Research and Material Command. The government has certain rights in the invention.

FIELD OF THE INVENTION OR TECHNICAL FIELD

The present invention relates to biomedical engineering, and, more particularly, to tissue engineering.

BACKGROUND OF THE INVENTION

In the United States, each year more than 700,000 people suffer from peripheral nerve injuries (PNI) that can lead to a lifelong disability, such as paralysis. The most frequent causes include motor vehicle accidents, gunshot wounds, stabbings, and birth trauma.

Currently, there are two gold standard treatments for nerve repair, which are end-to-end suturing and application of autograft or allograft biological tissue. However, each strategy suffers from a number of limitations. For example, end-to-end suturing cannot be performed when the nerve gap is larger than 1 cm. The use of autograft results in potential donor site morbidity for the patient and can potentially exacerbate the condition. The use of allograft tissue has an associated risk of immunogenicity.

Recent advances in tissue engineering and biomaterials suggest that there may be other approaches to nerve repair and regeneration that may overcome the limitations associated with harvesting natural tissues. One such approach would be the use of biomaterials to produce natural or synthetic nerve guidance conduits (NGCs). These NGCs may overcome some of the limitations of nerve autograft and allograft methods. The NGCs act as an essential precursor for nerve repair, since they can reduce tension at the suture line, can protect the regenerating axons from the infiltrating scar tissue, and can exhibit a low immune response. Although FDA-approved tissue engineered nerve devices have been available in the market for several years, these implant devices do not possess the proper physical topography or chemical cues for nerve repair and regeneration. Also, most of them are currently limited to a critical nerve gap of approximately 4 cm. To design an optimal NGC for enhancing PNR still remains a challenge.

Current laboratorial NGCs developed using haptotactic strategies alone are not yet comparable to autograft. For example, multichannel NGCs may have an insufficient cross sectional area and or inhibit cell-cell interaction between each of the individual channels. This may lead to functional mismatches and an insufficient level of regeneration. Controlling the position of inner filament bundles within NGCs has yet to be achieved, despite the fact that the presence of microfilaments has been demonstrated to enhance axonal regeneration and provide contact guidance for the regenerating axons in rats. Alternatively, microfilaments can mislead cell migration which can result in uneven distribution of cells within the NGC. These failures in NGCs may be attributed to the inadequate design of intra-luminal guidance channels/filament, forming incomplete fibrin cables during the initial stages of regeneration. Without the formation of this aligned bridge of extracellular material (ECM), further mechanisms for nerve repair are limited. Therefore, it still remains a challenge to design an optimal NGC for enhancing PNR, when compared to the use of autografts.

SUMMARY OF THE INVENTION

An embodiment of the present invention provides a fabricated implantable NGC. In some embodiments, the NGC comprises an inner spiral structured porous sheet. In some embodiments, the NGC comprises multiple inner spiral-structured porous sheets and/or multiple substantially cylindrical porous sheets. Such conduits have the potential to serve as medical devices to treat PNI and restore function to the site of the injury. This may be achieved by the spiral structure's ability to facilitate regeneration of nerve tissues.

In another embodiment of the present invention, the NGC has an integrated spiral structured porous sheet decorated with surface channels, multiple spiral structured porous sheets decorated with surface channels and/or multiple substantially cylindrical porous sheets decorated with surface channels. Such structures increase the surface area available for cell migration and attachment, and may reduce the length of time needed for recovery. Additionally, such structures can reduce the wear and tear that is often observed with single lumen tubular NGCs. A highly-aligned set of electrospun fibers are present within the surface channels, and may also be present on the backs thereof. The presence of aligned fibers in such areas ensures that the regenerating nerve will come into contact with aligned fibers.

In order to place and suture the nerve tissue without tension, there are two reserved chambers at the proximal and distal ends of the conduit. The chambers allow for nerve stumps to be sutured without tension because the chambers provide space to house the nerve in place with an optimal grip. An outer tube comprising a dense layer of randomly-oriented fibers can greatly improve the mechanical properties of the NGC and provides integrated structural support for nerve regeneration. The NGC and its component parts are tunable such that their length and diameter can be varied controllably depending on how the NGC is to be used. The method of fabricating the NGC does not limit its length, thus enabling the application for longer gap repair/regeneration for PNI.

BRIEF DESCRIPTION OF FIGURES

FIG. 1 is a schematic illustration in cutaway view of a nerve guidance conduit (NGC) according to a first embodiment of the present invention bridging the stumps of a damaged nerve;

FIG. 2 is a schematic end-on cross-sectional view of the NGC of FIG. 1;

FIG. 3 is a scanning electomicrograph (SEM) image of a first side of a portion of a porous polymeric sheet of a type used to fabricate NGCs according to an embodiment of the present invention;

FIG. 4 is an SEM image of the side opposite the first side of the porous polymeric sheet of FIG. 3;

FIG. 5 is an SEM image of a porous polymeric sheet having aligned nanofibers thereupon according to an embodiment of the present invention;

FIG. 6 is an SEM image of a porous polymeric sheet having randomly-distributed nanofibers thereupon;

DETAILED DESCRIPTION OF THE INVENTION

Figure 7:
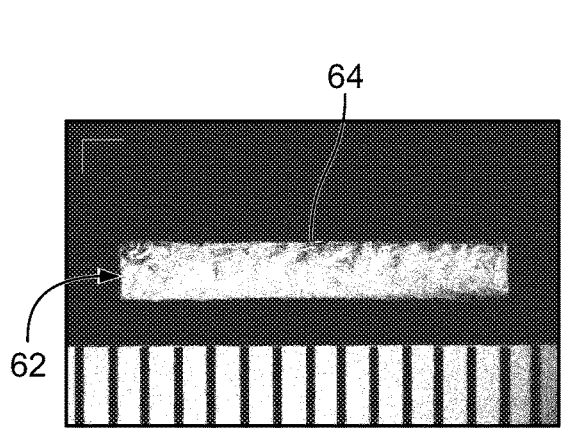
FIG. 7 is a stereomicroscopic image of the exterior of a second NGC according to the first embodiment of the present invention.

The following disclosure is presented to provide an illustration of the general principles of the present invention and is not meant to limit, in any way, the inventive concepts contained herein. Moreover, the particular features described in this section can be used in combination with the other described features in each of the multitude of possible permutations and combinations contained herein.

All terms defined herein should be afforded their broadest possible interpretation, including any implied meanings as dictated by a reading of the specification as well as any words that a person having skill in the art and/or a dictionary, treatise, or similar authority would assign thereto.

Further, it should be noted that, as recited herein, the singular forms "a", "an", and "the" include the plural referents unless otherwise stated. Additionally, the terms "comprises" and "comprising" when used herein specify that certain features are present in that embodiment, however, this phrase should not be interpreted to preclude the presence or additional of additional steps, operations, features, components, and/or groups thereof.

Embodiments of the present invention provide NGCs with integrated spiral structured porous sheets and/or substantially cylindrical porous sheets decorated with electrospun fibers. In some embodiments, the sheets are decorated with surface channels and electrospun fibers. In some embodiments, the electrospun fibers are aligned with each other, with the longitudinal axis of the NGC, and/or the surface channels. Such NGCs provide superior mechanical strength compared to NGCs in the prior art, along with integrated multiple channels, stable aligned fibrous layers, good inter-cell communication, and high surface/volume ratios within the NGCs. Chambers at the distal and proximal ends of the NGC provide additional space for fitting nerve stumps in order to reduce the tension at the suture line between the NGC and the nerve stump. A dense outer fibrous tube can prevent the infiltration of scar tissue into the NGC while the regeneration process takes place. One embodiment of the NGC of the present invention comprises an NGC having two chambers within the ends thereof.

In a first embodiment of the present invention, the NGC has a spiral guidance channel, the spiral structure including a highly porous polycaprolactone (PCL) sheet, which may be formed as a spiral-wound sheet using known methods and decorated with surface channels on a surface of the spiral wound sheet, coated with a thin layer of aligned electrospun fibers on the surface channels, and a dense randomly-oriented fibrous tube on the outside of the NGC. Other bioresorbable materials known for use in the biomedical arts may be used in place of PCL for the sheet and fibers (e.g., collagen/PCL blends for the fibers).

In a second embodiment of the present invention, the NGC has multiple spiral or cylindrically wound structures within a dense randomly-oriented fibrous tube. The spiral or cylindrically wound structures which may be formed as a spiral-wound sheet using known methods. The spiral or cylindrically wound structures may include multiple grooves along the spiral wall and, in some embodiments, in the inner wall of the fibrous tube. The wound structures and/or the inner wall of the fibrous tube, may also be decorated with nanofibers and/or other micro-architectural features that improve cell adhesion and control the direction of nerve regeneration, and make a more favorable environment for nerve regeneration. Methods of making micro-architectural features in polymer sheets and other polymer structures are known in the art. Other bioresorbable materials known for use in the biomedical arts may be used in place of PCL for the sheet and fibers (e.g., collagen/PCL blends for the fibers).

Other embodiments of the present invention provide processes for fabricating implantable NGCs, such as the embodiments of NGCs described above, which can be used as a medical device for facilitating the repair and regeneration of nerve tissues.

Several features of NGCs according to embodiments of the present invention are discussed herein below.

1. Three-Dimensional (3-D) Integrated Spiral Structured Porous Sheet with Proximal and Distal Reserved Chambers Collagen tubes, which have been approved by the FDA, lack sufficient mechanical strength to support nerve regeneration. As for multi-channel NGCs, the major drawback is that cells/axons in each channel do not interact well with those in the other channels, which adversely affects nerve regeneration and would affect nerve function recovery even if the nerve gap were bridged. In comparison, the integrated spiral structure makes the NGC of the present invention superior to those in the prior art in that mechanical properties are greatly improved and favorable for inter-cellular interaction and neural myelination. This is important for nerve regeneration because of the time required for nerve regeneration to bridge large nerve gaps. Further, a NGC should have enough mechanical strength to provide structural support to the nerve during regeneration. Also, the proximal and distal chambers in the ends of the NGC provide an optimal initial environment for nerve ingrowth. These chambers can prevent stress from accruing when the nerve tissue is sutured with the conduit in an end-to-end fashion. Moreover, the increased surface/volume ratio and the highly porous intermediate layers of the PCL sheet are preferred for cell attachment and nutrient transportation during nerve regeneration.

2. Decorated Surface Channels on the Spiral Porous Sheet with Additional Electrospun Aligned Fibers and an Outer Fibrous Tube Electrospinning is an approach for polymer biomaterial processing that provides an opportunity to control morphology, porosity and composition of an NGC using relatively unsophisticated equipment. Unlike conventional fiber spinning processes that produce fibers with diameters in the micrometer range, electrospinning is capable of producing fibers in the nanometer diameter range, which are typically deposited in the form of nonwoven fabrics. Nanofibers provide a connection between the nanoscale and the macroscale world, since, although their diameters are in the nanometer range, the fibers are very long, sometimes having lengths of the order of kilometers. A major problem of all hollow tubes is misdirection of cellular migration: since transected axons produce axon sprouts proceeding in a distal direction, a neuroma is always formed which consists of minifascicles proceeding in an abnormal manner, proliferating Schwann cells (SCs), fibroblasts and capillaries. If there is a directional factor of any kind (e.g., an artificial nerve tube which usually provides no endoneurial structure), the neuroma proceeds in the desired direction. This phenomenon has been called "neuromateous neurotization". In consequence, only a few dispersed axons are able to enter the right fascicle and endoneurial tube in the distal nerve stump once they have reached the end of the conduit in the interior of the NGC.

One successful tissue engineering strategy for nerve repair is to create aligned features on the conduit to provide guidance for cell migration and directional axonal regeneration across the glial scar and lesion site in both central nervous system and peripheral nervous system injuries. Such features may include aligned surface channels and electrospun fiber-based conduits for nerve repair, according to embodiments of the present invention.

Consequently, the construction of a spiral and/or cylindrically structured conduit with highly aligned surface channels and nano-fibers is very helpful for nerve proliferation and neurite extension. Meanwhile, the intricate aligned structure can also influence the growth and distribution of seeded SCs, which further directs the longitudinal extension of the neural axons. Further, there is a wide range of polymers available that are suitable for deposition on the spiral sheet to meet the individualized specifications for the NGC (e.g., collagen/PCL copolymer nanofibers, rather than pure PCL sheets).

Fibers spun along the outside of the NGC not only assist in stabilizing the spiral structure, but also inhibit infiltration of scar tissue through the inter-connected pores. By increasing the mechanical strength of the NGC, the risk of structural failure can be minimized, promoting more uniform and natural regeneration of nerve tissue.

Tunable Features of the NGC

In order to solve the conflict between optimizing the mechanical properties of the NGC and maximizing its length, many techniques may be used to reinforce the NGC. In a method according to an embodiment of the present invention, a spiral conduit (e.g., a spiral structured porous sheet) is placed onto a rotator and a nanofiber is spun in random orientations along the spiral structure to form an outer fibrous tube. The thickness of the outer fibrous tube can be controlled. This dense layer of randomly-oriented fibers deposited on the outside of the spiral conduit can improve the mechanical properties of the entire structure, and meanwhile provide a stable structural support during nerve regeneration. In a method according to an embodiment of the present invention, depositing the outside layer of fibers on the spiral conduit is the final and separate step of fabricating the NGC, so it is practical to modify the polymers used to form the fibers before the electrospinning step. The outer fibrous tube can be made from polymers that are different from that of the spiral sheet or the aligned fibers. In other embodiments, a tubular shell of randomly-oriented fibers is formed by spinning fibers onto a rotating rod, then removing the rod. One or more spiral or cylindrically structured conduits are then inserted into the tubular shell.

In another aspect, the process of the present invention is tunable in that the sizes of the spiral conduit are controllable, and both the length and the outside diameter are dependent on the size of the spiral-wound sheet. Therefore, in order to fabricate a spiral conduit with a particular size, (e.g., a length larger than 15 mm, which is the maximum length of nerve regeneration achieved with silicone tubes in rats), it is only necessary to cut a polymer sheet to the appropriate size.

Embodiments of the Present Invention

I. Implantable Nerve Guidance Conduit Having a Single Spiral Wound Channel

FIG. 1 is a schematic illustration in cutaway view of a nerve guidance conduit (NGC) 10 according to a first embodiment of the present invention bridging the stumps 12, 14 of damaged nerve 16. The stumps 12, 14 are received in reserved chambers 18, 20 at the proximal and distal ends 22, 24 of the NGC 10, and held in place with sutures 26, 28, or by other means known in the art. The reserved chambers 18, 20 allow the nerve stumps 12, 14 to be placed in the NGC 10 and sutured without tension by housing the nerve stumps 12, 14 in place with an optimal grip.

FIG. 2 is a schematic cross-sectional view of the NGC 10 showing that the NGC 10 includes an outer fibrous tube 30 surrounding one or more spiral wound sheets 32 The fibrous tube 30 includes a dense structure of randomly oriented polymer fibers (not shown). The spiral wound sheets 32 define a lumen 34 inside the NGC 10. The lumen 34 is bounded by an inner surface 36 of the spiral wound sheets 32. The NGC 10 further includes an integrated guidance spiral 38 having a plurality of surface channels 40. The guidance spiral 38 is are composed of multiple layers (e.g., layers 42, 44), and together define a spiral guidance channel 46 within the lumen 34. In some embodiments of the present invention, the surface channels 40 are arranged such that they are substantially parallel to each other and to a longitudinal axis (not shown) of the NGC 10. The layers 42, 44 may be extensions of the spiral-wound sheets 32, or may be formed separately therefrom, then integrated with the spiral-wound sheets 32. The plurality of surface channels 40 increases the surface area of the guidance spiral 38 that is available for cell migration and may reduce the length of time needed for nerve regeneration. Additionally, the integrated layers 42, 44 may reduce the wear and tear that can occur in NGCs known in the art. Such wear and tear is often observed with single lumen tubular NGCs.

In some embodiments of the present invention, a highly aligned orientation of electrospun nanofibers (not shown) are provided as coats on the surface channels 40, and on both layers 42, 44 of the spiral sheet 38, and dense randomly-oriented fibers are provided on an outer surface 48 of the NGC 10, which greatly improves the mechanical properties of the NGC 10, as discussed above. In some embodiments, the aligned fibers are substantially parallel to each other. In some embodiments, the aligned fibers are substantially parallel to a longitudinal axis of the NGC 10. The presence of aligned fibers ensures that all areas of the regenerating axon will come into contact with aligned fibers.

The NGC 10 is tunable such that its size can be varied in a controlled fashion depending on how it is to be used. The length and the outer diameter of the NGC 10 are dependent on the size of guidance spiral 38. An NGC 10 according to the present invention may have any length, thus enabling it to be used to repair long gaps in the axon for the repair or regeneration of peripheral nerves.

FIGS. 3 and 4 are scanning electromicrograph (SEM) images a first side and a second side opposite the first side of a portion of a porous polymeric sheet 50 of a type that may be used to fabricate the spiral-wound sheets 32 or guidance spiral 38 of an NGC of the same type as NGC 10, before the application of electrospun nanofibers. Interconnected pores (e.g., pores 52) are present throughout the polymeric sheet 50. FIG. 5 is an SEM image of a porous polymeric sheet 54 of the same type as polymeric sheet 50, showing aligned nanofibers 56 that have been deposited on the polymeric sheet 54 by electrospinning. FIG. 6 is an SEM image of a porous polymeric sheet 58 of the same type as polymeric sheets 50, 54 showing randomly-distributed nanofibers 60 that have been deposited on the polymeric sheet 58 by electrospinning.

Figure 8:
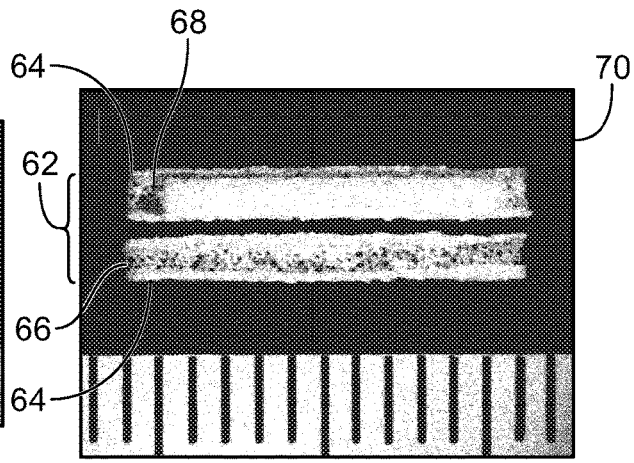
FIG. 8 is stereomicroscopic image of the NGC of FIG. 7 after being sectioned longitudinally.
Figure 9:
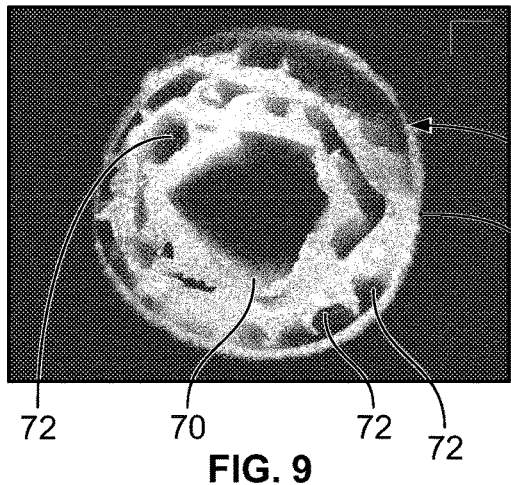
FIG. 9 is a stereomicroscopic image of an end-on view of the NGC of FIG. 7.
Figure 10:
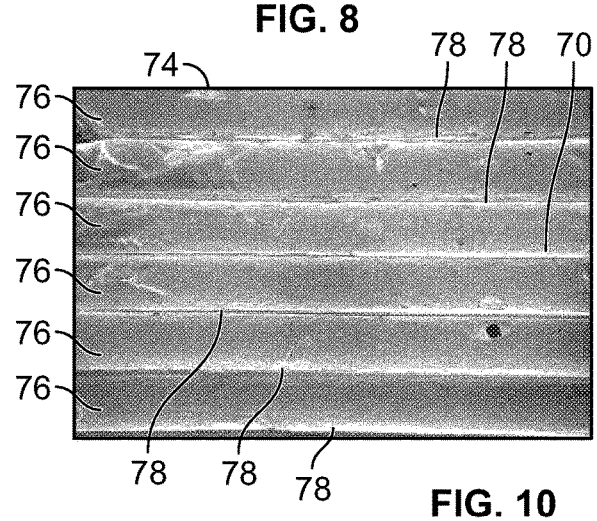
FIG. 10 is an SEM image of surface channels on a polymer sheet of a type used to fabricate an NGC according to embodiments of the present invention.

FIGS. 7-9 are stereomicroscopic images of an NGC 62 according to an embodiment of the present invention. NGC 62 is of the same general type as the NGC 10 discussed with respect to FIGS. 1 and 2. FIG. 7 is an image of the intact NGC 62 showing its outer fibrous tube 64. FIG. 8 is an image of the interior of the NGC 62 after it has been cut lengthwise, showing an interior surface 66 of the outer fibrous tube 64, the guidance spiral 66, and the reserved chambers 68, 70. FIG. 9 is an end view of the NGC 62 showing the outer spiral wall 64, the guidance spiral 66 and the channels 72 of the guidance spiral 66. FIG. 10 is a SEM image of a portion of polymer sheet 74, which is of a type for making an NGC according to an embodiment of the present invention, showing the substantially parallel alignment of channels 76, which are separated by ridges 78.

Exemplary Fabrication Method

In a method of fabricating an NGC according to an embodiment of the present invention, a polycaprolactone (PCL) sheet was fabricated using a combination of the solvent evaporation method and the salt-leaching method. An 8% (w/v) PCL solution was poured onto a glass petri dish, and acupuncture needles having a diameter of 150 μm were placed on top of the PCL solution to form multi-channels having widths of about 180 μm. The dish was moved to a hood to let it air dry. After an hour, the resulting PCL sheet was immersed into deionized water so that the salt was dissolved, producing pores in the PCL sheet. The needles were also removed, having formed multi-channels on the PCL sheet with widths of about 180 μm. After 30 minutes, the PCL sheet was taken out and dried on a paper towel. Subsequently, 2 hours later, the fully dried PCL sheet was cut into a rectangular shape having dimensions of about 12 mm by 10.5 mm to bridge a 10 mm nerve gap in an animal study.

Figure 11:
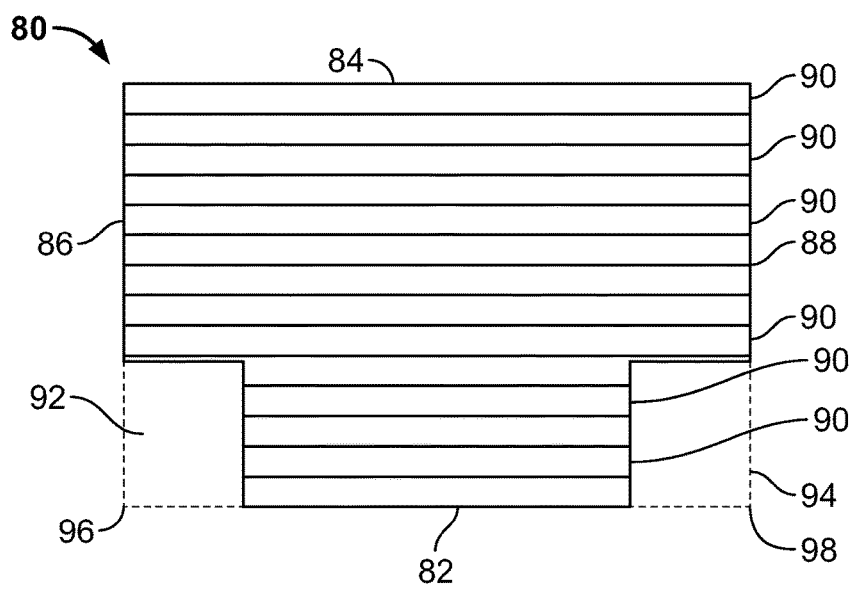
FIG. 11 is a schematic diagram of a polymer sheet of the type shown in FIG. 10.

Referring to FIG. 11, in an exemplary embodiment of the method, the cut PCL sheet 80 had opposite longer edges 82, 84 (i.e., the 12 mm edges), and opposite shorter edges 86, 88 (i.e., the 10.5 mm edges). It may be noted that the channels 90 are substantially parallel to the longer edges 82, 84. Two rectangular areas 92, 94 were cut out from the opposite corners 96, 98 of the edge 82, such that edge 82 was then shorter than edge 84.

PCL aligned nanofibers were spun on the cut PCL sheet 80 using a conductible rotation disk method known in the art. A 16% (w/v) solution of PCL in 1,1,1,3,3,3 Hexafluoroisopropanol (HFIP) (Oakwood Products, Inc) was prepared for electrospinning. Aligned fibers were deposited on the 12 mm×10.5 mm PCL sheet longitudinally on the edge of the rotating disk such that the fibers were substantially parallel to channels 90. The fibers were deposited such that they would be substantially longer than the cut PCL sheet 80. The sheet was carefully removed from the disk to ensure the fibers deposited remained aligned. The excess lengths of fiber (i.e., the portions of the fibers that extended beyond the edges of the cut PCL sheet 80 were collected and folded onto the back of the cut PCL sheet 80.

Turning back to FIG. 11, the cut PCL sheet 80 with the aligned nanofibers thereon was then wound in a spiral fashion from the edge 82 to the edge 84, such that the edge 82 was in the interior of the resulting spiral NGC and the channels 90 were substantially parallel to a longitudinal axis of the spiral NGC. In the spiral NGC, the cutaway areas 92, 94 become reserved chambers (e.g. reserved chambers 68, 70 of spiral NGC 64 of FIGS. 7-9, or reserved chambers 18, 20 of spiral NGC 10 of FIG. 1).

Random nanofibers were then spun onto the outside of the spiral NGC to form an outer fibrous tube on the spiral NGC. The thickness of the outer fibrous tube was approximately 150 μm. The outer fibrous tube is intended to secure the entire spiral structure, enhance the mechanical strength, and prevent tissue infiltration during nerve regeneration. The resulting spiral NGC with its outer fibrous tube was 1.8 mm in diameter and 12 mm in length, suitable for bridging a 10 mm nerve gap.

Tensile Properties of the NGCs of the Present Invention

Figure 12:
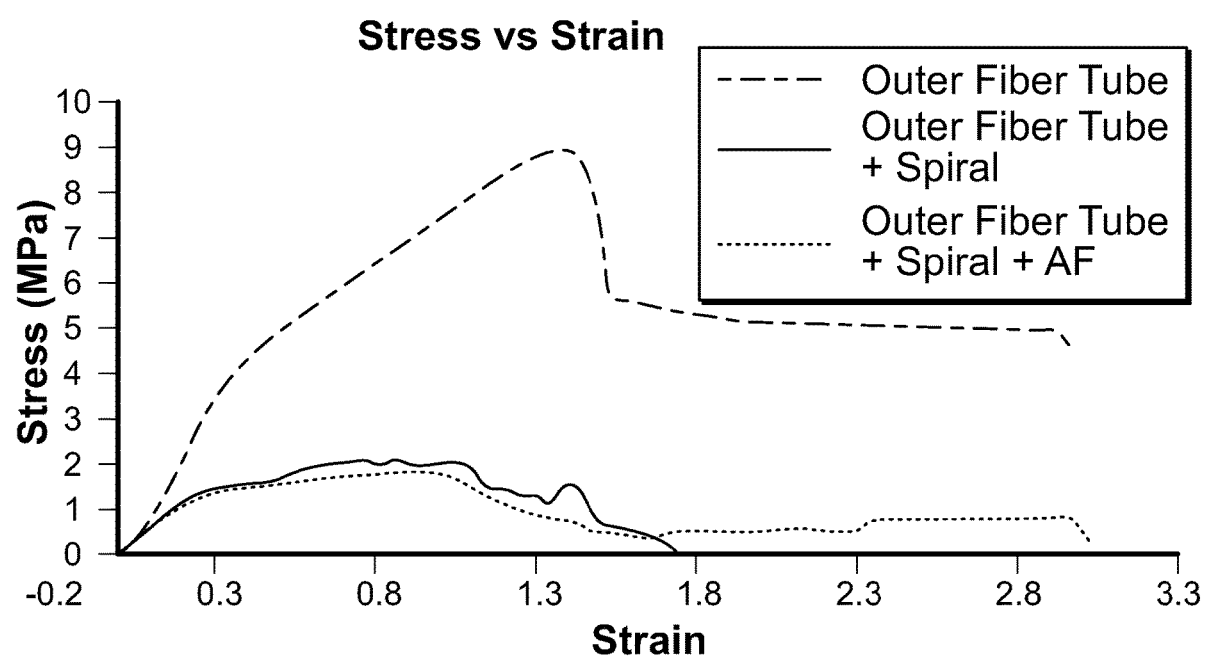
FIG. 12 is a group of stress-strain plots generated from tests performed on various NGCs which are embodiments of the present invention.

FIG. 12 is a plot of stress versus strain for several NGCs fabricated according to a method of the present invention: an outer fiber tube comprising a dense layer of randomly-oriented nanofibers; the outer fiber tube with a spiral sheet therein, and the outer fiber tube with the spiral sheet and aligned nanofibers ("AF"). The following tensile properties were measured: Young's Modulus, percent elongation to failure, and tensile strength of the different NGCs. The Young's Modulus, calculated through the stress-strain curve shown FIG. 12, ranged between 0.262-0.7625 Mpa. All three of the NGCs yielded a Young's Modulus that can stand force stretching and be applicable for in vivo use. The values reported for the outer fibrous tube and the other NGCs all in a useful range for use in nerve regeneration and repair. High tensile strength will provide a mechanically strong NGC that can be sutured well during coaptation of the nerve stump and NGC, and preserve the suture after surgery. The measured physical properties of the NGCs of FIG. 11 are summarized in Table 1, below.

TABLE 1

Tensile Properties of Nerve Guidance Conduits

| | Young's Modulus (MPa) | % Elongation | Tensile Strength (MPa) |
|---|---|---|---|
| Outer Fibrous Tube | 0.7625 | 296.4 | 8.98 |
| Outer Fibrous Tube + Spiral | 0.33766 | 171 | 2.08 |
| Outer Fibrous Tube + Spiral + AF | 0.32766 | 301 | 1.78 |

Porosities of the NGCs

The measured porosity values for the outer fibrous tube (hereinafter, NGC-T), outer fibrous tube+spiral (hereinafter, NGC-T-S), and outer fibrous tube+spiral+AF (hereinafter, NGC-T-S-AF) were respectively 71.98±1.22%, 75.01±2.69%, and 78.41±3.64%. The differences in porosities for these three types of NGCs are not statistically significant (p<0.05).

Cell Proliferation

Figure 13:
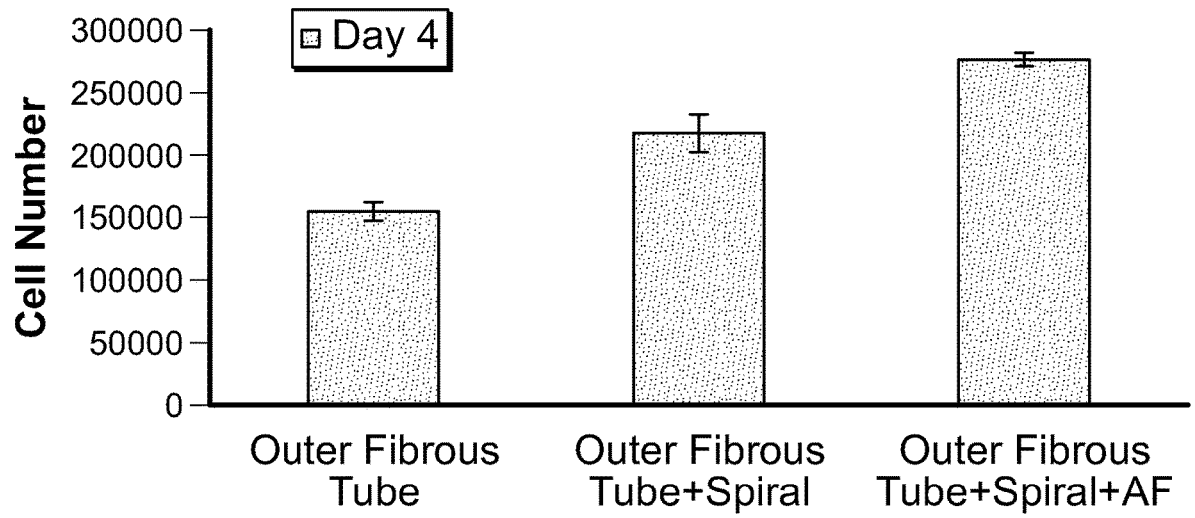
FIG. 13 is a bar chart comparing cell proliferation on various NGCs which are embodiments of the present invention.

Schwann cells were adopted as the model for evaluation of cellular response on the fiber-based spiral NGCs. At day 4, NGC-T-S-AF showed significantly greater cell proliferation than NGC-T and NGC-T-S. The cell numbers for each type of NGC are shown in FIG. 13. The degrees of cell proliferation for the NGC-T and NGC-T-S are significantly lower (p<0.05) than for the NGC-T-S-AF.

Implantation and Testing of NGCs

Figure 14:
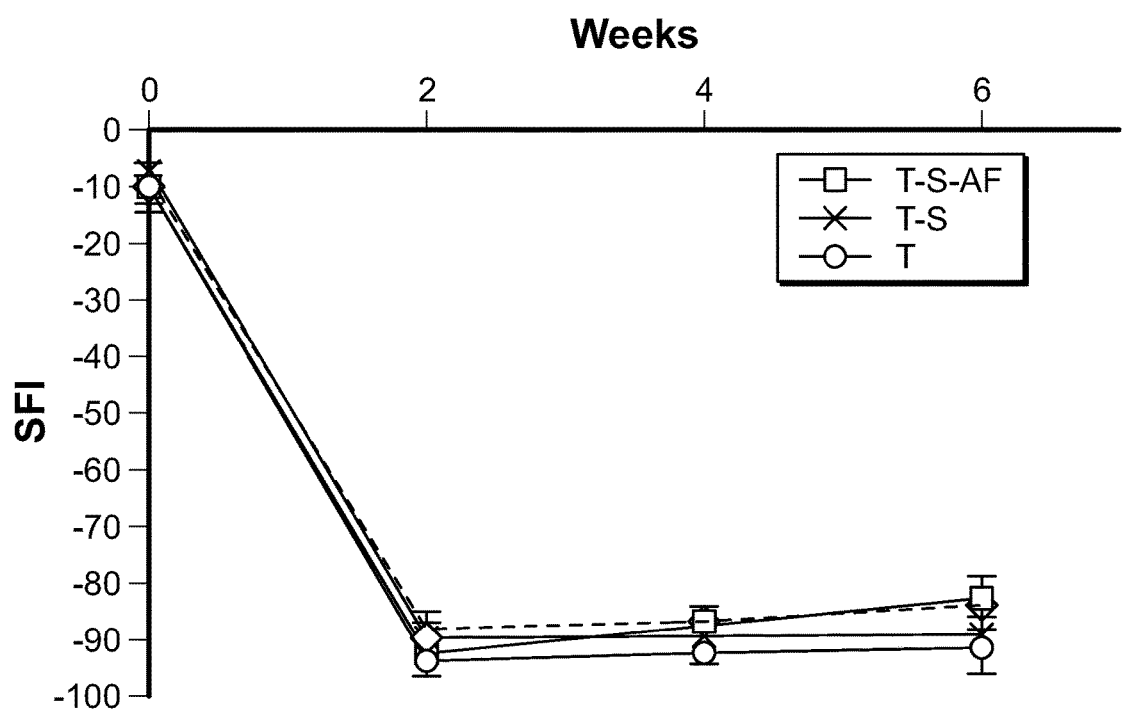
FIG. 14 is a plot showing changes in sciatic functional index (SFI) over time for rats having implanted NGCs according to embodiments of the present invention.

The NGCs were tested in a 10 mm Sprague Dawley (SD) rat sciatic nerve defect to evaluate the effect of nanofibers on peripheral nerve regeneration through porous spiral NGCs. The sciatic nerve of each rat was cut, then bridged with one of the NGCs. One group received an autograft rather than a NGC. One group received no grafts. All rats were in good condition during the survival weeks. There were no obvious signs of systemic or regional inflammation and surgical complications after implantation The recovery of motor function was assessed based on the walking track evaluation Referring to FIG. 14, normal sciatic functional index (SFI) value of −9.4±1.4 was measured from all healthy rats (n=30) before surgery. All experimental animals had decreased SFI of values between −85.6 and −94.5 (n=30) by week 2 after surgery. During the initial 4 weeks, there was no significant improvement in any of the groups. At 6 weeks after surgery, the overall SFI reached the levels between −72.2 and −91.7, which was equivalent to an improvement of 2.8-13.4 index points from week 2. Each group's 6-week SFI value was recorded as follows: autograft (−72.2±6.6), T-S-AF (−81.5±3.2), T-S (−88.4±4.9), and T (−91.7±4.2). The autograft SFI revealed a significant difference (p<0.05) as compared to the T-S and T groups. The SFI in the T-S-AF group was significantly higher than for the T groups (p<0.05).

Figure 15:
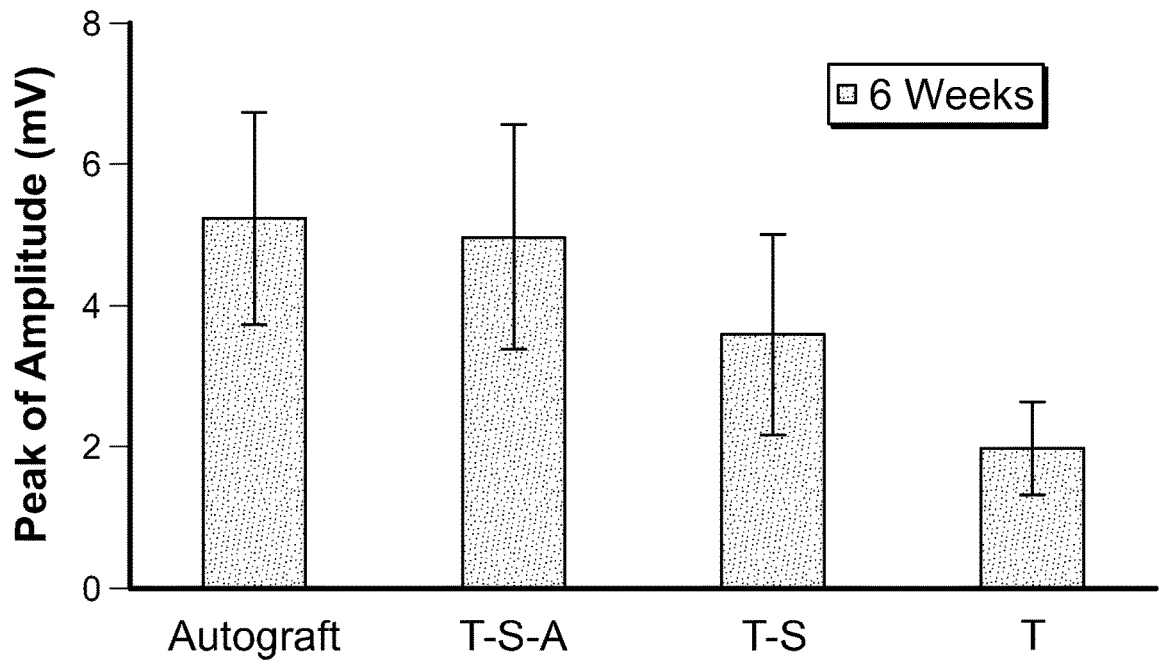
FIG. 15 is a bar chart of compound muscle action potentials (CMAP) for rats having implanted NGCs according to embodiments of the present invention.
Figure 16:
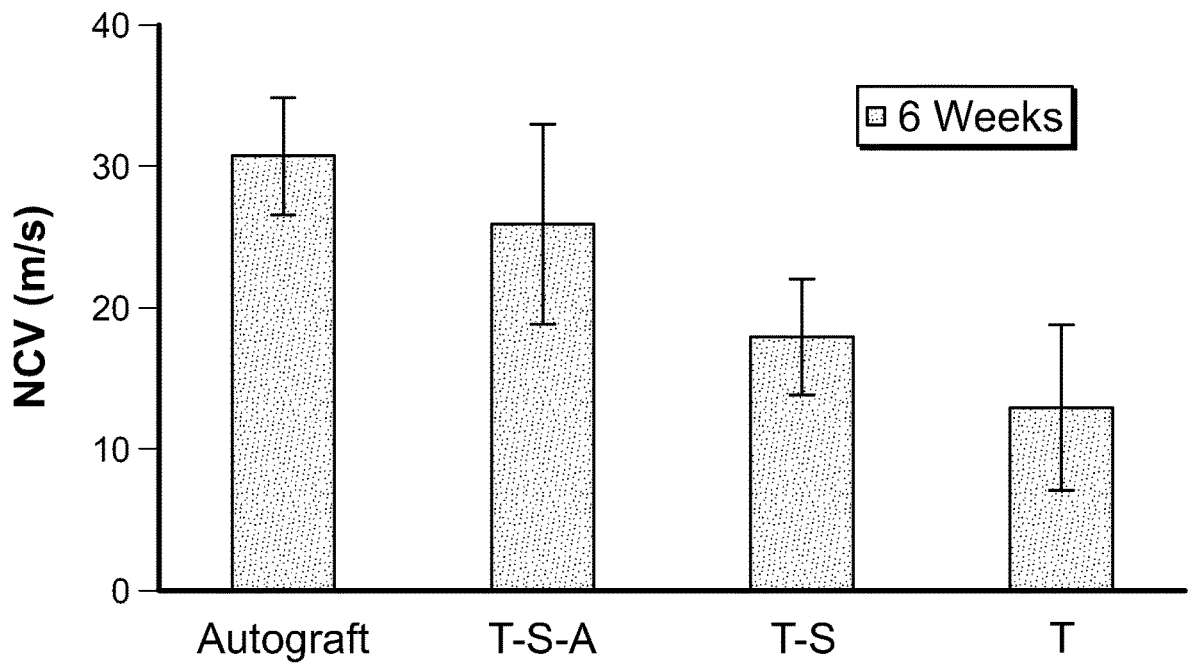
FIG. 16 is a bar chart of nerve conduction velocities (NCV) for rats having implanted NGCs according to embodiments of the present invention.

Functional recovery was further evaluated with electrophysiological assessment to determine whether functional recovery occurred through the NGCs. Six weeks post-surgery, compound muscle action potentials (CMAP) were evoked by stimulation at the surgical limbs and recorded from gastrocnemius muscle following by measurements of amplitude and nerve conduction velocity (NCV). Signals were absent and no muscle contractions were observed in the non-grafted group. Referring to FIG. 15, for the amplitude measurements, each group's value was recorded as follows: autograft (5.25±1.51 mV), T-S-AF (4.96±1.58 mV), T-S (3.6±1.39 mV), and T (2.0±0.64 mV). Significant differences in amplitude were observed in the T group as compared to the autograft and T-S-AF groups (p<0.05). However, the difference between the autograft, T-S-AF, and T-S groups (p>0.05) was not statistically significant. Similar results were found in NCV measurement: autograft (31.57±4.13 m/s), T-S-AF (26.47±6.87 m/s), T-S (18.28±4.16 m/s), and T (13.3±5.65 m/s) (See FIG. 16). Significant differences in NCV were observed in the autograft group as compared to the T-S and T groups (p<0.05). The NCV result in the T group also showed a significant difference as compared to autograft and T-S-AF groups (p<0.05). However, there were no significant differences when the NCV values of the autograft group were compared to those of the T-S-AF group, which may indicate that nanofibers can accelerate the level of muscle reinnervation as well as autograft.

After 6 weeks post-surgery, the distal nerve segment from each group was explored and carefully isolated from the surrounding tissues. A pinch reflex test was performed distally. A reflex movement of the back muscles indicates that the sensory fibers are positively regenerated through the NGCs, while no movement was considered as lack of sensory fibers in the NGCs. The results are presented in Table 2, below.

TABLE 2

Pinch Test Results

| | Number of rats responding to pinch test (n = 5) |
|---|---|
| Autograft | 5/5 |
| T-S-AF | 5/5 |
| T-S | 4/5 |
| T | 3/5 |

Further histological evaluations of nerve regeneration behavior with NGCs were investigated under a light microscope. The results clearly demonstrated the potential of the NGCs of the present invention to house a large number of supportive cells, both with and without nanofibers to enhance the surface area of the channel. The NGCs possessed durable mechanical strength to support the entire regeneration process. Low magnifications of micrographs showed that neural tissues, including myelinated axons and myelin sheath, were all successfully presented among the groups. Angiogenesis occurred through which new blood vessels were formed during the nerve regeneration process. Normal axons were nearly all surrounded by uniform thicknesses of myelin sheaths and presented large fiber diameters. Nevertheless, the studied groups presented premature morphologies (i.e., diverse nerve fiber sizes and thinner myelin sheaths).

Figure 17:
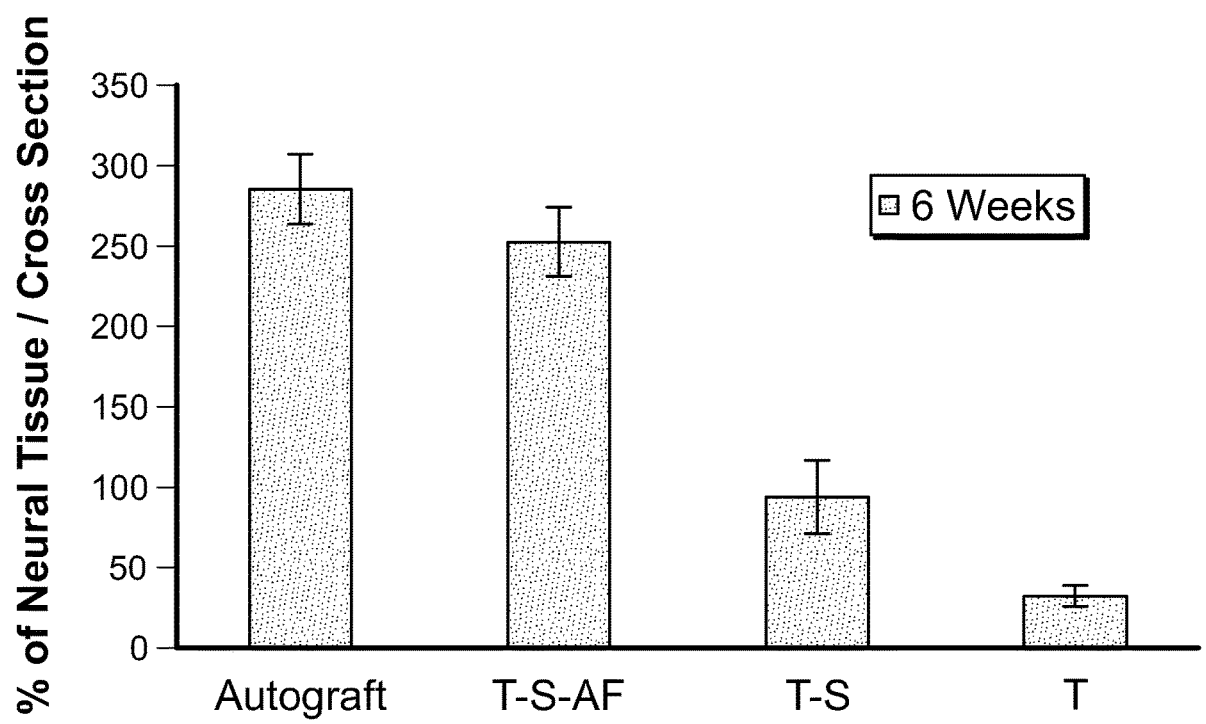
FIG. 17 is a bar chart of percent of neural tissue regenerated in sciatic nerves bridged by NGCs according to embodiments of the present invention.

Quantitative analysis of the total occupied neural tissue coverage in the NGCs compared to those of normal rat nerves (70.57±3.81%) further confirmed the above findings. Referring to FIG. 17, each group's value was recorded as follow: autograft (29.29±4.61%), T-S-AF (26.52±3.77%), T-S (17.37±2.97%), and T (5.88±1.43%). No significant differences were found among autograft and T-S-AF groups. However, the area occupied by neural tissue in T-S group showed significantly lower values than the autograft, and T-S-AF groups. High significance was observed in the T group as compared to the other groups (p<0.01). Finally, it should be noted that the cross-sectional micrograph of T group was covered with a large white area. That implied the single lumen repair limited the nerve regeneration.

Figure 18:
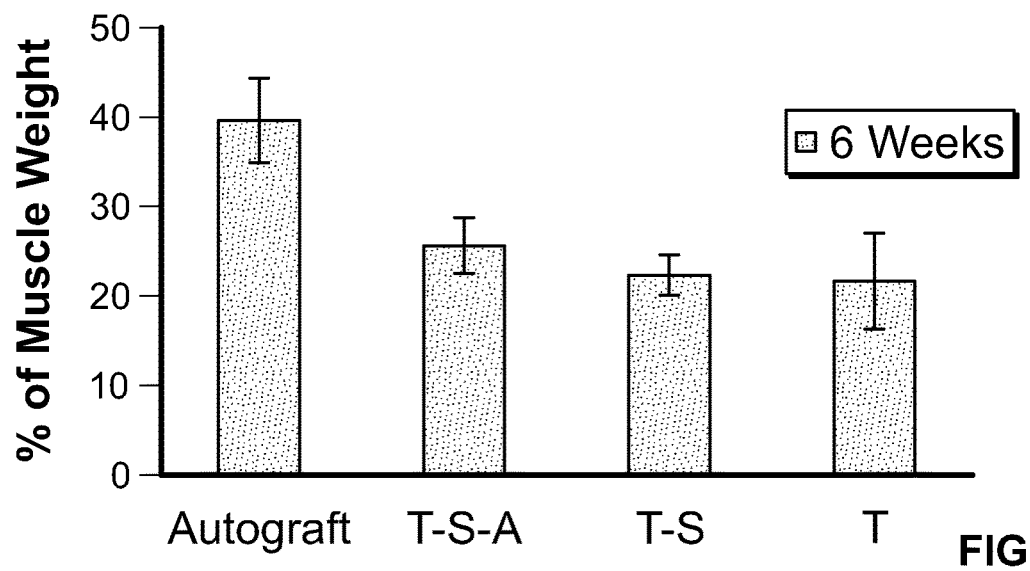
FIG. 18 is a bar chart comparing muscle weight ratios for the gastrocnemius muscle of rats for which the sciatic nerve was bridged by NGCs according to embodiments of the present invention.

When severe nerve injury occurs, the muscle is denervated and the balance of muscle metabolism could be shifted from protein synthesis toward protein degradation. As a consequence, the target muscle presents a decreased muscle cell size, muscle weight loss, hyperplasia of connective tissues, and new blood vessel formation. To evaluate the reinnervation of the gastrocnemius muscle, Masson trichrome staining was applied to the section followed by measurements of muscle weight ratio, diameter of muscle fibers, and muscle fiber coverage per cross section. Referring to FIG. 18, for comparisons of muscle weight ratio, each group's value was recorded as follows: autograft (39.73±4.19%), T-S-AF (25.64±3.01%), T-S (22.31±2.18%), and T (19.2±2.03%). The muscle weight ratio of the autograft group was greater than that of the other groups by a statistically significant amount (p<0.05). However, there were no significant differences between the T-S-AF and T-S groups (p>0.05). The T group revealed a significant lower ratio than the T-S-AF group.

Figure 19:
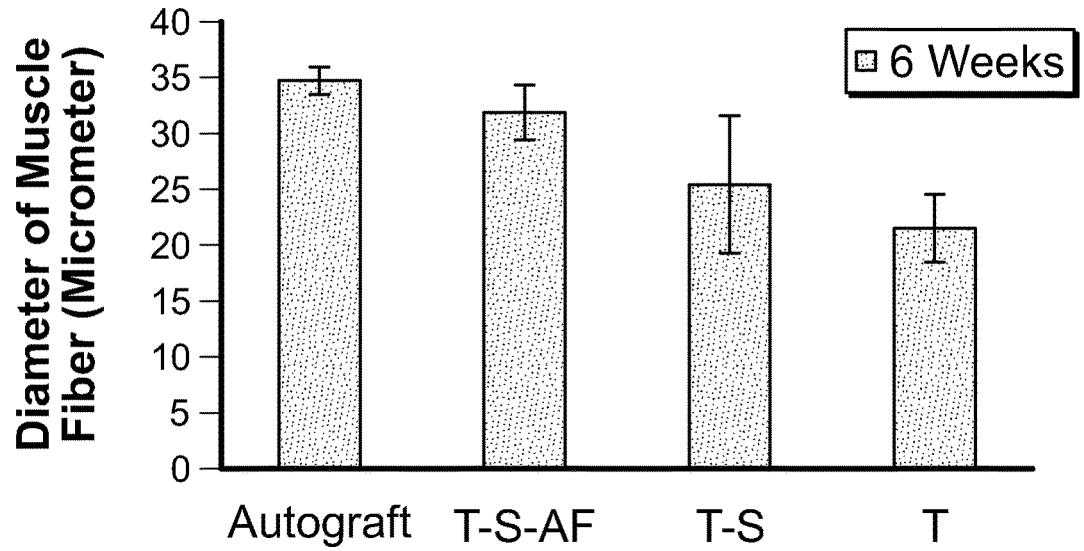
FIG. 19 is a bar chart comparing muscle fiber diameter for the gastrocnemius muscle of rats for which the sciatic nerve was bridged by NGCs according to embodiments of the present invention.

Referring to FIG. 19, for comparisons of muscle fiber diameter, each group's value was recorded as follows: autograft (34.62±1.05 μm), T-S-AF (31.81±2.18 μm), T-S (25.5±6 μm), and T (21.56±2.98 μm). Although the autograft group showed a significant difference from the T-S and T groups, it was not significantly higher than the T-S-AF group. Also, there were no significant differences between the T-S and T groups (p>0.05). Further findings showed that the value for the T group was significantly lower than that for the autograft, and T-S-AF groups.

Figure 20:
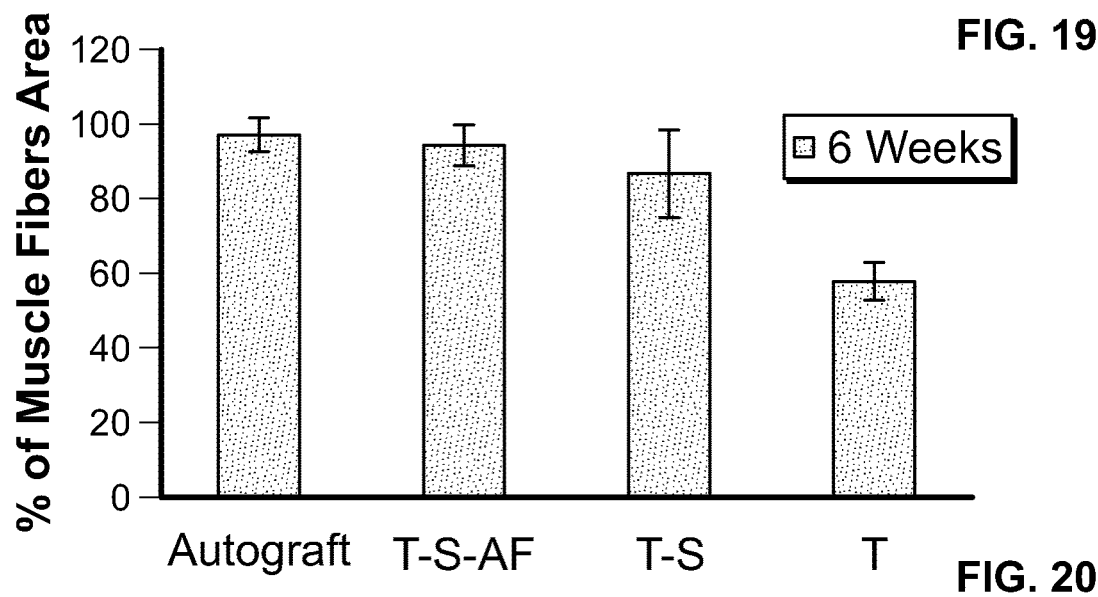
FIG. 20 is a bar chart comparing muscle fiber coverage for the gastrocnemius muscle of rats for which the sciatic nerve was bridged by NGCs according to embodiments of the present invention.

Referring to FIG. 20, for comparisons of muscle fiber coverage, each group's value was recorded as follows: autograft (96.84±4.1%), T-S-AF (93.72±4.63%), T-S (86.99±10.31%), and T (58.42±4.69%). There were no significant differences between the values for the autograft, T-S-AF, and T-S groups (p>0.05); however, they were all significantly greater than the value for the T group (p<0.05).

From qualitative analyses and histological observations discussed above, spiral NGCs of the present invention, with or without nanofibers, revealed the potential to prevent muscle atrophy as well as the effect of autograft. Both the surface channels and the aligned fibers provide good topographical cues for nerve regeneration, and thus allow muscle reinnervation faster than single lumen NGCs, thus suggesting that the surface channels and nanofibers further assisted NGC structures in promoting nerve regeneration.

II. Implantable Multi-Spiral Nerve Guidance Conduit

Figure 21:
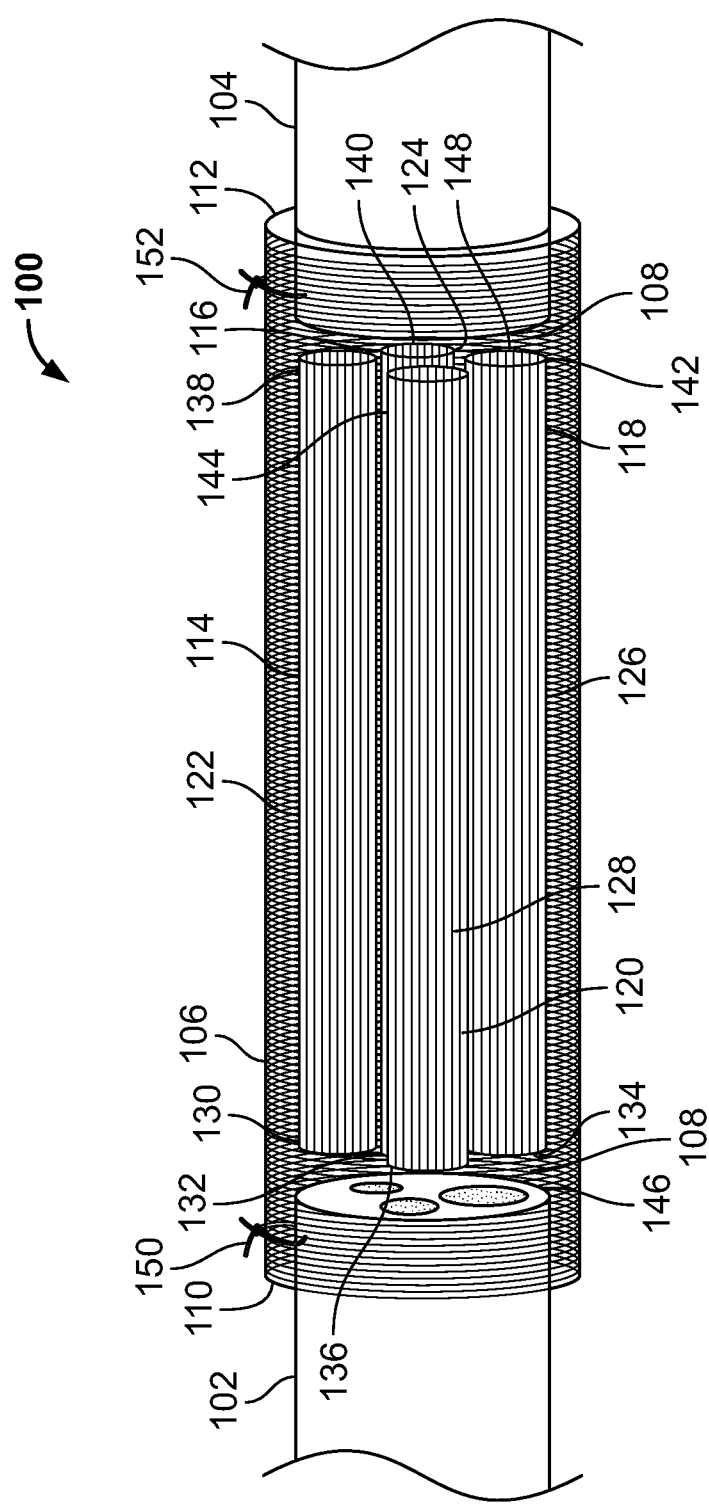
FIG. 21 is a schematic illustration in cutaway view of a NGC according to a second embodiment of the present invention bridging the stumps of a damaged nerve.

FIG. 21 is a schematic illustration in cutaway view of a nerve guidance conduit (NGC) 100 according to a second embodiment of the present invention bridging the stumps 102, 104 of a damaged nerve. The NGC 100 includes a fibrous tube 106 that defines a lumen 108 therein, and has a first end 100 and a second end 112 opposite the first end 100 along a longitudinal axis (not shown) of the NGC 100. The NGC 100 further includes a plurality of guidance channels 114, 116,118, 120 inside of fibrous tube 106. The guidance channels 114, 116, 118, 120 are porous, being formed of porous polymeric sheets 122, 124, 126, 128 of the same general type as porous polymeric sheets 50, 54 discussed above with respect to NGC 10. The guidance channels 114, 116, 118, 120 have respective first ends 130, 132, 134, 136 and respective second ends 138, 140, 142, 144 opposite the respective first ends 130, 132, 134, 136 along respective longitudinal axes (not shown). The guidance channels 114, 116, 118, 120 are shorter than the fibrous tube 106, and reside entirely within the fibrous tube 106 with the respective first ends 130, 132, 134, 136 of the guidance channels 114, 116, 118, 120 aligned with each other, and the respective second ends 138, 140, 142, 144 of the guidance channels 114, 116, 118, 120 aligned with each other.

Continuing to refer to FIG. 21, the nerve stumps 102, 104 are received in reserved chambers 146, 148 at the first end 110 and second end 112, respectively, of the NGC 100, and held in place with sutures 150, 152 or by other means known in the art. The first reserved chamber 146, in which nerve stump 102 is received, is defined by the respective first ends 130, 132, 134, 136 of the guidance channels 114, 116, 118, 120 and the first end 110 of the fibrous tube 106. The second reserved chamber 148, in which the nerve stump 104 is received, is defined by the respective second ends 138, 140, 142, 144 of the guidance channels 114, 116, 118, 120 and the second end 112 of the fibrous tube 106. The reserved chambers 146, 148 are arranged to receive, house, and grip the nerve stumps 102, 104 within the lumen 108 of the fibrous tube 106, whereby the NGC 100 bridges a gap between the nerve stumps 102, 104 and prevents stress from accruing in the nerve stumps 102, 104 when the nerve stumps 102, 104 are attached to the NGC 100 by sutures 150, 152 or by other means known in the art.

Figures 22, 23:
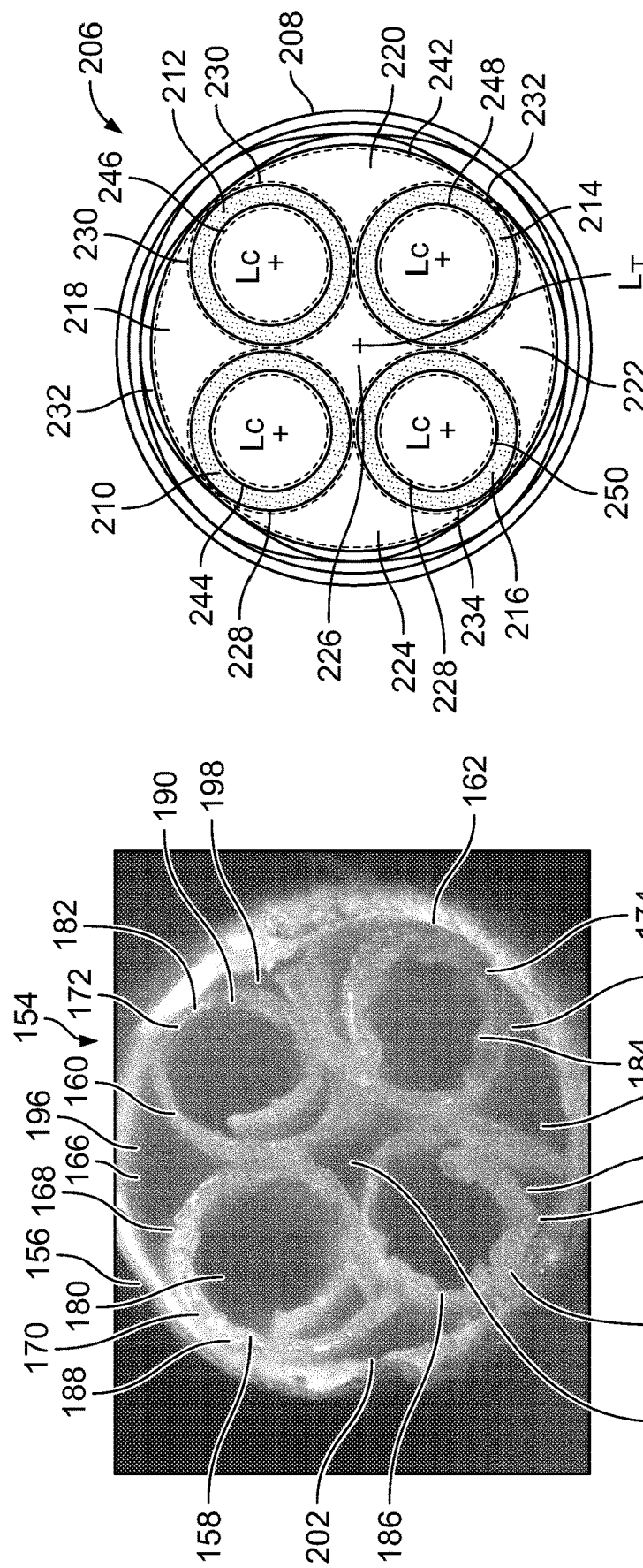
FIG. 22 is an end-on cross-sectional view of an NGC according to the embodiment of FIG. 21.
FIG. 23 is a schematic illustration of an end-on cross-sectional view of an NGC of the same general type as the NGCs illustrated in FIGS. 22 and 23.

FIG. 22 is an end-on cross-sectional view of an NGC 154 of the same type illustrated schematically in FIG. 21. FIG. 22 shows the fibrous tube 156 surrounding multiple guidance channels 158, 160, 162, 164. The fibrous tube 156 includes a dense structure of randomly oriented polymer fibers (not shown). The lumen 166 is bounded by an inner surface 168 of the fibrous tube 156. The guidance channels 158, 160, 162, 164 are formed by porous polymer sheets 170, 172, 174, 176 of the same general type as the porous polymer sheets 50, 54 discussed with respect to NGC 10. The porous polymer sheets 170, 172, 174, 176 are rolled to form guidance channels 158, 160, 162, 164, each guidance channel having an inner surface 180, 182, 184, 186 and an outer surface 188, 190, 192, 194 opposite the inner surface 180, 182, 184, 186. In an embodiment, the plurality of guidance channels 158, 160, 162, 164 are arranged to define additional guidance channels 196, 198, 200, 202, 204 bounded by the outer surfaces 188, 190, 192, 194 of the guidance channels 158, 160, 162, 164 or by the outer surfaces 188, 190, 192, 194 of the guidance channels 158, 160, 162, 164 and the inner surface 168 of the fibrous tube 154.

In the embodiment of FIG. 22, the guidance channels 158, 160, 162, 164 have spiral cross-sections. In an embodiment, the guidance channels of an NGC (not shown) of the same general type as NGC 154 have cross-sections that are circular or substantially circular. In an embodiment, the guidance channels in an NGC of the same general type as NGC 154 include structures other than porous polymer sheets, such as fibrous tubes (not shown) arranged to fit within fibrous tube 156.

FIG. 23 is a schematic illustration of an end-on cross-sectional view of an NGC 206 of the same general type as the NGCs 100, 154 illustrated in FIGS. 22 and 23. FIG. 23 shows the outer fibrous tube 208 surrounding multiple guidance channels 210, 212, 214, 216, which define additional guidance channels 218, 220, 222, 224, 226 bounded by the outer surfaces 228, 230, 232, 234 of the guidance channels 210, 212, 214, 216 or by the outer surfaces 228, 230, 232, 234 of the guidance channels 210, 212, 214, 216 and the inner surface 236 of the fibrous tube 208.

The NGC 206 illustrated in FIG. 23 includes highly aligned electrospun nanofibers seen in FIG. 23 in an end-on view. For clarity, nanofibers 238, 240, 242, which are representative of all of the nanofibers in FIG. 23, are labeled in lieu of labeling all of the nanofibers in FIG. 23. In an NGC according to embodiments of the present invention, nanofibers may be present on any or all of the inner surfaces of the guidance channels, the outer surfaces of the guidance channels, and the inner surface of the fibrous tube. In the exemplary NGC of FIG. 23, the nanofibers 238, 240, 242 are present on the inner surfaces 244, 246, 248, 250 and outer surfaces 228, 230, 232, 234 of the guidance channels 210, 212, 214, 216, and the inner surface 236 of the fibrous tube 208, respectively. The nanofibers 238, 240, 242 are in alignment with each other and with the longitudinal axes Lc of the guidance channels 210, 212, 214, 216 and the longitudinal axis LT of the fibrous tube 208. In the view presented in FIG. 23, longitudinal axes are denoted by the symbol "+", and would project out of the page. The presence of the aligned nanofibers 238, 240, 242 on all of the aforementioned surfaces ensures that all areas of the regenerating axon will come into contact with aligned nanofibers.

The NGC 100, 154, 206 is tunable such that its size can be varied in a controlled fashion depending on how it is to be used. The length and outer diameter of the NGC 100, 154, 206 may be selected to bridge a gap of a known length between the stumps of a nerve, and to provide reserved chambers that receive, house, and grip the nerve stumps within the lumen of the fibrous tube, whereby the NGC bridges a gap between the nerve stumps. An NGC 100, 154, 206 according to the present invention may have any length, thus enabling it to be used to repair long gaps in the axon for the repair or regeneration of peripheral nerves. The diameter of the NGC and/or the number of guidance channels may be varied to accommodate nerve stumps having different sizes and positions. The exemplary embodiments of nerve guidance conduits of the present invention that are discussed in relation to FIGS. 21, 22, and 23 have four guidance channels within the outer tubes. In other embodiments of the present invention, the nerve guidance conduits have fewer than four guidance channels or more than four guidance conduits, depending on the size and location of the nerve that is to be bridge by the nerve guidance conduit, and on the mechanical and regenerative properties that are desired for the nerve guidance conduit.

Exemplary Fabrication Method

Preparation of the PCL Sheet

In a method of fabricating an NGC according to an embodiment of the present invention, a polycaprolactone (PCL) sheet was fabricated using a combination of the solvent evaporation method and the salt-leaching method. Briefly, to make a monolayer of salt pre-coated glass petri dish (Daigger), 1 ml of 20% (w/v) glucose solution was pipetted onto a glass petri dish and incubated in 70° C. oven until the glucose became sticky.

After 20 minutes, the petri dish was taken out of the oven and salt particles having nominal diameters of less than 106 μm were added to form a thin monolayer. The petri dish was dried under a fume hood at room temperature and then stored in a desiccator for further use. 6 ml of 10% (w/v) PCL/DCM solution was spread on the salt pre-coated glass petri dish to form a PCL sheet. The DCM was then evaporated under the fume hood to form a dry PCL layer. Two hours later, the petri dish was transferred to the desiccator for further drying, and left overnight. In order to detach the dried PCL sheet from the glass petri dish, thee PCL sheet was fully covered with 5 ml of deionized water. Once the PCL sheet separated from the dish, it was relocated to a 500 ml beaker containing 400 ml of deionized water to remove the remaining salt. About one day of salt leaching provided a highly porous PCL sheet having a thickness of about 100 μm.

Preparation of the Nanofibrous Coating

The porous PCL sheet was cut into several rectangular sheets (15 mm×2 mm). PCL aligned nanofibers were collected on the 15 mm×2 mm rectangular sheets by electrospinning, using an aluminum rotating disk collector as a mount for the rectangular sheets. Briefly, 16% PCL (640 mg Mn-80,000; Sigma-Aldrich) was dissolved in 4 ml of hexafluoroisopropanol (HFIP) (Oakwood Products, Inc.) at room temperature. For the electrospinning process, 1 ml of PCL solution was poured into a 5.0 ml BD plastic syringe (Becton-Dickinson) with a 20 gauge flat-tip (Fisher) for generating fibers. The needle was connected to a high-voltage power supply (Gamma High Voltage Research; Ormond Beach, Fla.) at 15 kV to charge the polymer solution. The distance from the needle tip toward the grounded rotating disk collector was fixed at 55 m. A syringe pump (Braintree Scientific Inc.) was placed perpendicular to the collector, and the flow rate of syringe pump was fixed at 0.25 ml/hr. The nanofibers were collected on the 15 mm×2 mm rectangular sheets, which had been attached on the edge of the rotating disk using a piece of double-sided tape (3M). The nanofibers are deposited such that they are aligned with one another, and that they will be parallel to the longitudinal axis of the fibrous tube in the assembled NGC. After 16 minutes of electrospinning, the 15 mm×2 mm rectangular sheets were removed from the rotating disk, and the aligned fibers are secured on both sides and within the dimensions of the sheet.

Preparation of the Outer Nanofibrous Tube

A dense layer of random PCL fibers was electrospun for 25 minutes onto a rotating stainless steel rod wrapped in aluminum foil spinning at a rate of 150 revolutions-per-minute (rpm) to form a single PCL fibrous tube. After 25 minutes, the aluminum foil was separated from the rod, and removed from the collected nanofibers to obtain a single PCL fibrous tube. Similar tubes were used in various embodiments of the NGC of the present invention, which were tested in a rat sciatic model. After drying, followed by removal of the stainless steel rod, the fibrous tube had an inner diameter of 1.6+ mm and a length of 17+ mm, useful for bridging a 15 mm gap in a severed sciatic nerve.

Preparation of the Multi-Spiral Channel NGC

Once the 15 mm×2 mm rectangular sheets were carefully removed from the disk collector, they were rolled into spiral structures on a copper rod or wire, and heated in an oven at 40° C. for 10 minutes, to form spiral channels that were 15 mm long with an inner diameter of 0.64 inches. The edges of the resulting tubes were sealed with dichloromethane (DCM). The rolling step is taken to ensure that the spiral channels are open structures allowing the regenerating nerves to enter the channels.

Four spiral channels were then inserted into the outer nanofibrous tube, where they fit tightly. The spiral channels resided within the fibrous tubes at depths of about 1 mm from each end of the fibrous tube. The fibrous tube permanently fixed the four spiral channels and enhanced the mechanical strength of the overall NGC. The spiral channels were further stabilized within the tube using DMC. For clinical applications, the NGC may have less than four channels or more than four channels to accommodate the sizes and positions of different nerves. The multiple spiral channels start and end at the same distances as each other within the fibrous tube so that the spiral channels remain stable within the fibrous tube. NGCs assembled in this fashion have been observed to remain in place for at least eight weeks during nerve regeneration, as by examination with a compound microscope prior to surgery and subsequent characterization testing.

The positioning of the four spiral channels created five additional channels defined by the outer surfaces of the spiral channels and the inner surface of the lumen of the fibrous tube. The space of about 1 mm between the ends of the spirals channels and the ends of the fibrous tube provided reserved chambers on either end of the NGC for insertion and attachment of nerve stumps.

Implantation and Testing of NGCs

The NGCs were tested in a 15 mm Sprague Dawley (SD) rat sciatic nerve defect to evaluate the effect of nanofibers on peripheral nerve regeneration through porous spiral NGCs. The sciatic nerve of each rat was cut, then bridged with one of the NGCs. One group received an autograft rather than a NGC. One group received no grafts. All rats were in good condition during the survival weeks. There were no obvious signs of systemic or regional inflammation and surgical complications after implantation.

Figure 24:
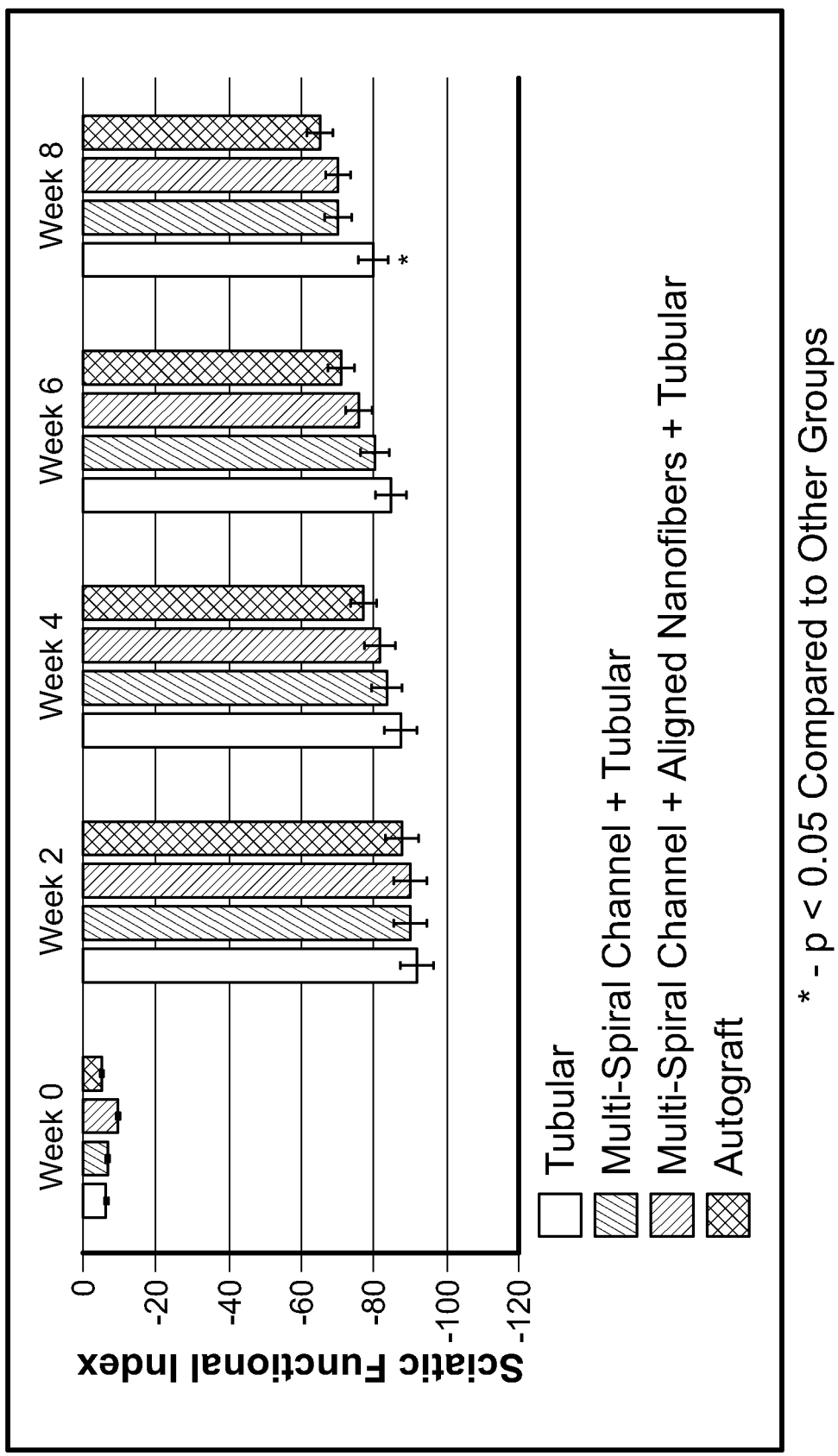
FIG. 24 is a bar chart showing changes in sciatic functional index (SFI) over time for rats having implanted NGCs according to embodiments of the present invention.

The recovery of motor function was assessed based on the walking track evaluation. Referring to FIG. 24, normal sciatic functional index (SFI) values were measured from all healthy rats (n=30) before surgery. All experimental animals had decreased SFI values by week 2 after surgery. During the initial 4 weeks, there was no significant improvement in any of the groups. The sciatic functional index (SFI) values for week 8 were: tubular was −80.2+7.7, multi-spiral channel+tubular group was −70.2+1.4, multi-spiral channel+aligned nanofibers+tubular −70.1+1.8, and autograft was −65.4+5. The tubular group was statistically worse than the other groups.

Figure 25:
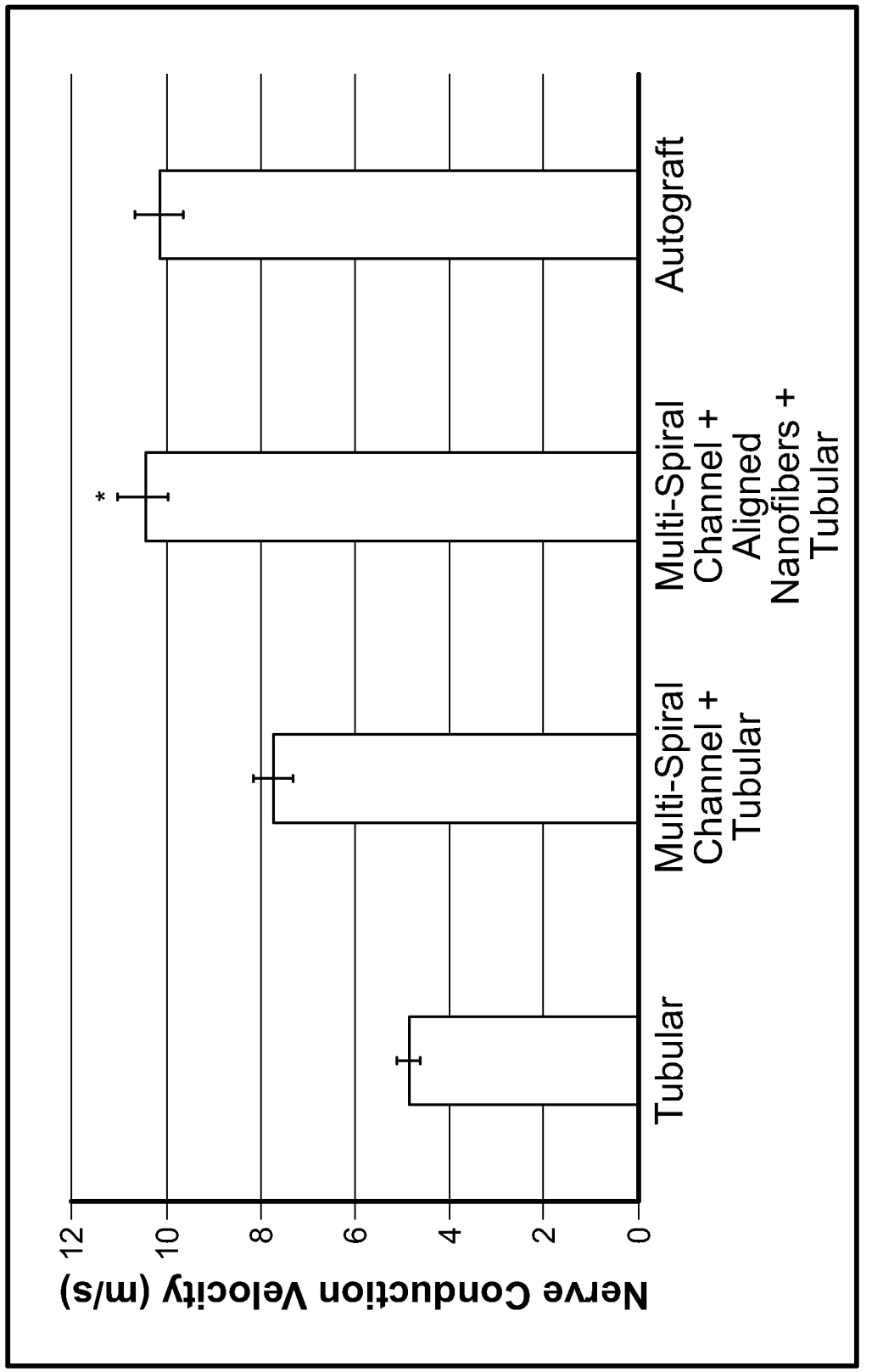
FIG. 25 is a bar chart of compound muscle action potentials (CMAP) for rats having implanted NGCs according to embodiments of the present invention.

Functional recovery was further evaluated with electrophysiological assessment to determine whether functional recovery occurred through the NGCs. Six weeks post-surgery, compound muscle action potentials (CMAP) were evoked by stimulation at the surgical limbs and recorded from gastrocnemius muscle following by measurements of amplitude and nerve conduction velocity (NCV). Signals were absent and no muscle contractions were observed in the non-grafted group. Referring to FIG. 25, for the amplitude measurements, each group's value was recorded as follows: tubular was 2.2+0.67 mV, multi-spiral channel+tubular group was 2.97+0.3 mV, multi-spiral channel+aligned nanofibers+tubular 3.79+0.92 mV, and autograft was 4.44+2.17 mV. The groups were all statistically comparable.

Figure 26:
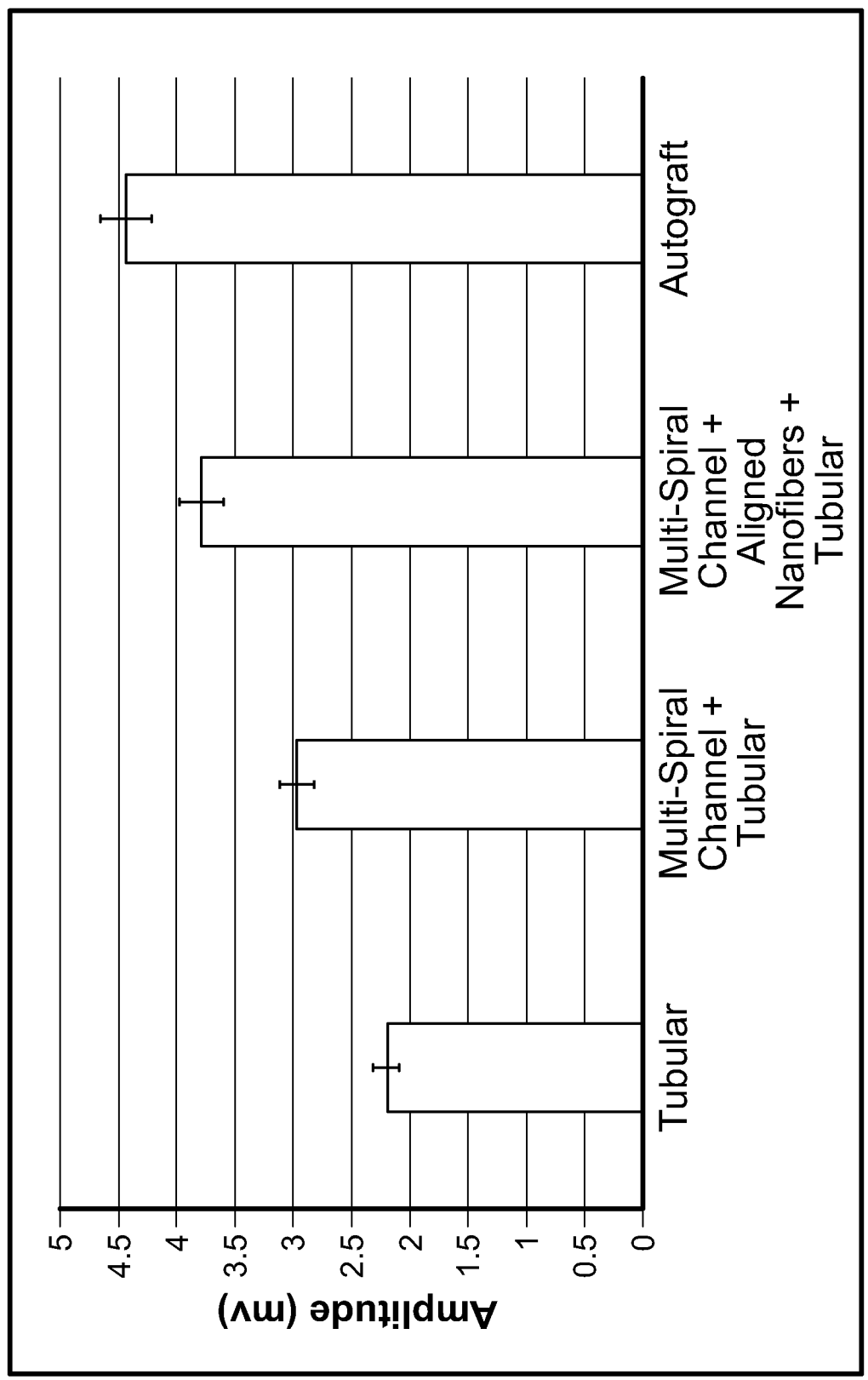
FIG. 26 is a bar chart of nerve conduction velocities (NCV) for rats having implanted NGCs according to embodiments of the present invention.

The results for the nerve conduction velocity (NCV) were: tubular was 4.86.2+0.45 m/s, multi-spiral channel+tubular group was 7.74+2.58 m/s, multi-spiral channel+aligned nanofibers+tubular 10.5+4.68 m/s, and autograft was 10.15+2.36 m/s (See FIG. 26). The multi-spiral channel+aligned nanofibers+tubular was statistically comparable to the autograft.

After 8 weeks post-surgery, the distal nerve segment from each group was explored and carefully isolated from the surrounding tissues. A pinch reflex test was performed distally. A reflex movement of the back muscles indicates that the sensory fibers are positively regenerated through the NGCs, while no movement was considered as lack of sensory fibers in the NGCs. The results are presented in Table 3, below.

TABLE 3

Pinch Test Results

| | Number of Rats Responding to Pinch Test |
|---|---|
| Tubular | 1/5 |
| Multi-spiral channel + T | 3/5 |
| Multi-spiral channel + AF + T | 4/5 |
| Autograft | 4/5 |

Figure 27:
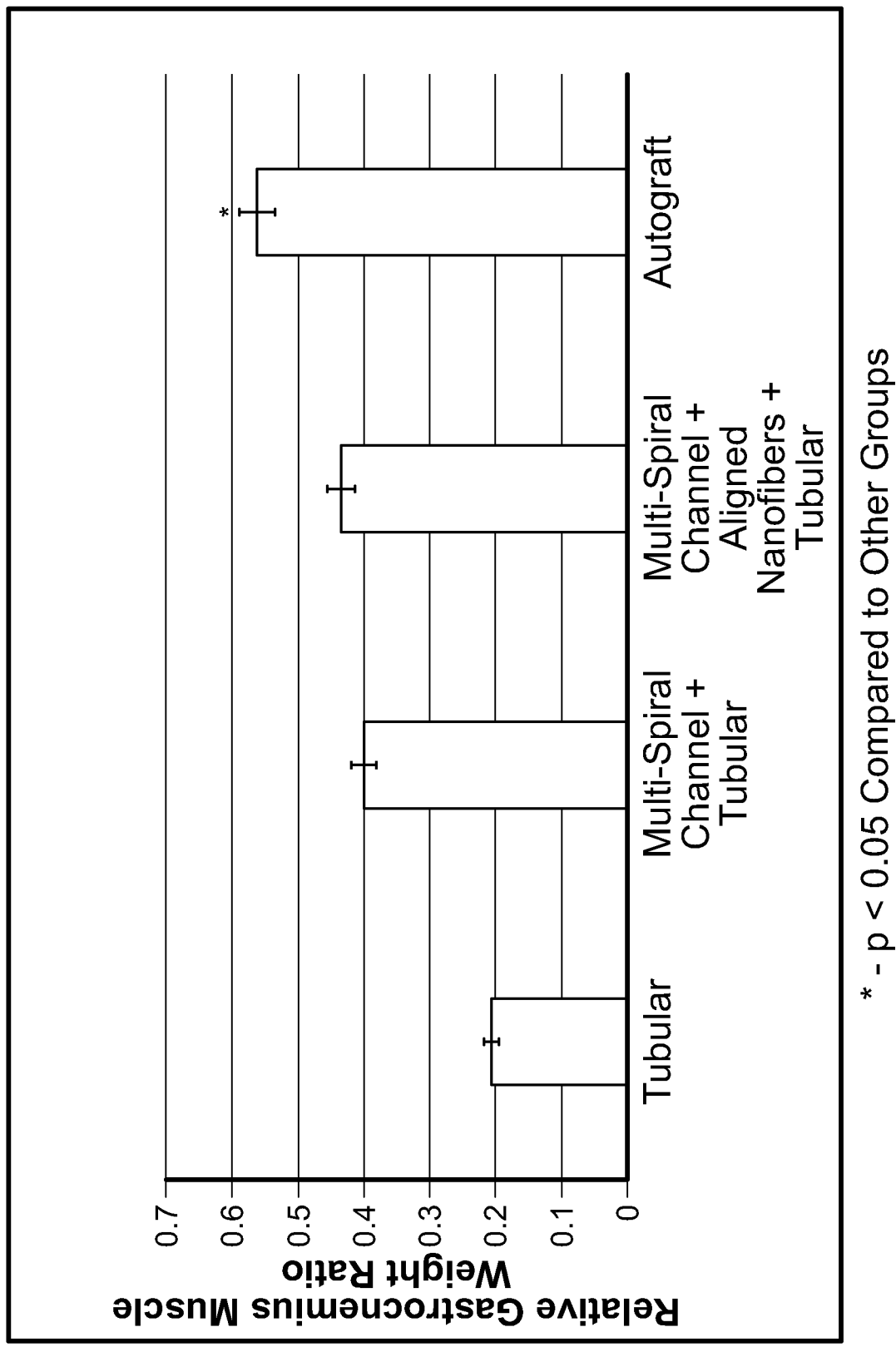
FIG. 27 is a bar chart comparing muscle weight ratios for the gastrocnemius muscle of rats for which the sciatic nerve was bridged by NGCs according to embodiments of the present invention.
Figure 28:
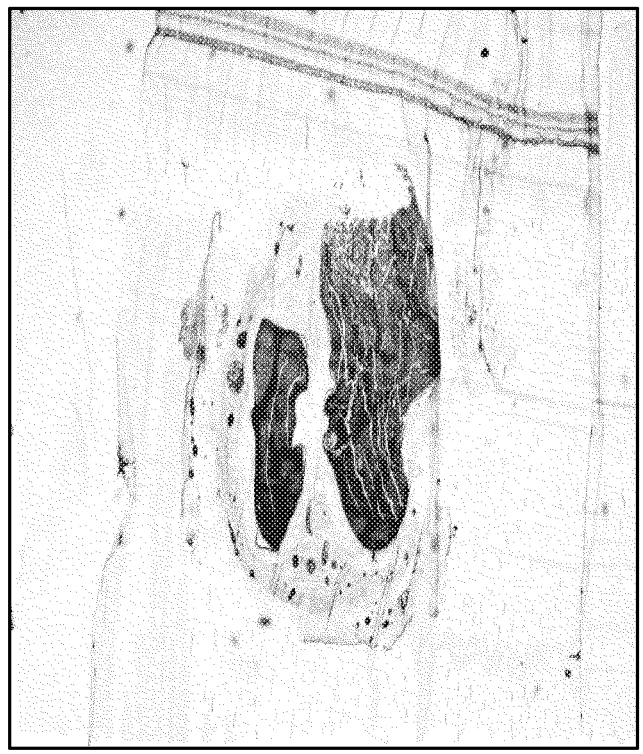
FIG. 28 is a histology image of an autograft of a sciatic nerve.
Figure 29:
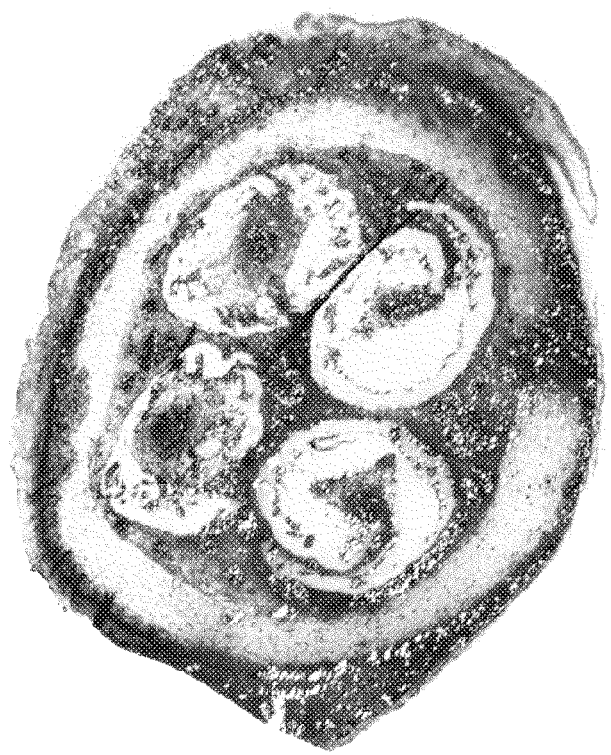
FIG. 29 is a histology image of a multi-spiral channel nerve guidance conduit constructed in accordance with the nerve guidance conduit of FIGS. 21-23.
Figure 30:
FIG. 30 is a histology image of a tubular nerve guidance conduit.

When severe nerve injury occurs, the muscle is denervated and the balance of muscle metabolism could be shifted from protein synthesis toward protein degradation. As a consequence, the target muscle presents a decreased muscle cell size, muscle weight loss, hyperplasia of connective tissues, and new blood vessel formation. To evaluate the reinnervation of the gastrocnemius muscle, it was removed from the ipsilateral side and contralateral side then weighed, the ratio of the former was taken with respect to the latter. Referring to FIG. 27, for comparisons of muscle weight ratio, each group's value was recorded as follows: tubular was 0.21+0.07, multi-spiral channel+tubular group was 0.4+0.06, multi-spiral channel+aligned nanofibers+tubular 0.43+0.14, and autograft was 0.56+0.16. The autograft statistically better than the remaining groups, which were comparable to each other.

It should be understood that the embodiments described herein are merely exemplary in nature and that a person skilled in the art may make many variations and modifications thereto without departing from the scope of the present invention. All such variations and modifications, including those discussed above, are intended to be included within the scope of the invention, as defined by the appended claims.

The invention claimed is:

1. A method of preparing a nerve guidance conduit, comprising the steps of:
    forming a porous sheet of biocompatible material by a solvent casting process;
    forming a plurality of substantially parallel surface channels on a surface of the porous sheet by applying parallel rods having micron-scale diameters to the biocompatible material during the solvent casting process;
    cutting the porous sheet into a shaped porous sheet having first and second edges opposite each other and substantially parallel to the surface channels;
    cutting rectangular pieces away from corners of the shaped porous sheet, the corners being at opposite ends of the first edge, such that the first edge is shorter in length from the second edge;
    depositing a first plurality of first nanofibers along the shaped porous sheet and the plurality of surface channels such that the first nanofibers are aligned with the plurality of surface channels and with each other in a substantially parallel arrangement;
    winding the shaped porous sheet into a spiral structure such that the first edge is within the spiral structure; and
    depositing a second plurality of second nanofibers around the outside of the spiral structure in random orientations, thereby forming a coating of second nanofibers around the spiral structure.

2. The method of claim 1, wherein the biocompatible material is polycaprolactone.

3. The method of claim 1, wherein the porous sheet has a plurality of pores.

4. The method of claim 3, wherein the pores are created in the porous sheet via a salt leaching step.

5. The method of claim 1, wherein each surface channel of the plurality of surface channels has a width of about 180 um.

6. The method of claim 1, wherein the first nanofibers are deposited along the shaped porous sheet via electrospinning.

7. The method of claim 1, wherein the second edge is on the outside of the spiral structure.

8. The method of claim 7, wherein the second nanofibers are deposited on the outside of the spiral structure via electrospinning.

9. The method of claim 1, wherein the second nanofibers form a fibrous tube extending about the spiral structure.

10. The method of claim 9, wherein the fibrous tube has a thickness of about 150 um.

11. The method of claim 1, wherein the spiral structure has a first end defined by one of the cut away corners of the shaped porous sheet and a second end defined by the other of the cut away corners of the shaped porous sheet.

12. The method of claim 11, wherein the first end of the spiral structure is located at one end of the nerve guidance conduit and the second end of the spiral structure is located at an opposite end of the nerve guidance structure.

13. The method of claim 12, wherein the first end of the spiral structure is configured to receive one stump of a severed nerve and the second end of the spiral structure is configured to receive another stump of the severed nerve.

14. The method of claim 11, wherein the plurality of surface channels extend from the first end of the spiral structure to the second end of the spiral structure.

15. The method of claim 11, wherein the spiral structure is wound such that it forms an internal guidance channel extending from the first end of the spiral structure to the second end of the spiral structure.

16. The method of claim 1, wherein the spiral structure is wound such that the surface channels are arranged on an outward oriented wall of the spiral structure.

17. The method of claim 16, wherein the spiral structure is wound such that it has a plurality of layers.

18. The method of claim 17, wherein the surface channels are provided on at least two of the layers forming the spiral structure.

19. The method of claim 18, further comprising the step of depositing a third plurality of nanofibers on inward oriented walls of at least two layers of the spiral structure.

20. The method of claim 16, further comprising the step of depositing a third plurality of nanofibers on an inward oriented wall of the spiral structure.

* * * * *